US012350522B2

(12) United States Patent
Alexis et al.

(10) Patent No.: US 12,350,522 B2
(45) Date of Patent: Jul. 8, 2025

(54) RADIOTHERAPY APPARATUS FOR DELIVERING RADIATION TO A SUBJECT

(71) Applicant: Elekta Limited, Crawley (GB)

(72) Inventors: Henrik Alexis, Crawley (GB); Kristian Wiberg, Crawley (GB)

(73) Assignee: Elekta Limited, Crawley (GB)

( * ) Notice: Subject to any disclaimer, the term of this patent is extended or adjusted under 35 U.S.C. 154(b) by 271 days.

(21) Appl. No.: 17/757,674

(22) PCT Filed: Dec. 17, 2020

(86) PCT No.: PCT/EP2020/086650
§ 371 (c)(1),
(2) Date: Jun. 17, 2022

(87) PCT Pub. No.: WO2021/122899
PCT Pub. Date: Jun. 24, 2021

(65) Prior Publication Data
US 2023/0031538 A1    Feb. 2, 2023

(30) Foreign Application Priority Data
Dec. 18, 2019  (GB) ..................... 1918753

(51) Int. Cl.
*A61N 5/10* (2006.01)
*A61B 6/00* (2024.01)
*A61B 6/04* (2006.01)
(52) U.S. Cl.
CPC .......... *A61N 5/1064* (2013.01); *A61B 6/0407* (2013.01); *A61N 5/1081* (2013.01); *A61B 6/5276* (2013.01)

(58) Field of Classification Search
CPC .. A61N 5/1081; A61N 5/1064; A61N 5/1069; A61N 5/1049; A61N 2005/1061;
(Continued)

(56) References Cited

U.S. PATENT DOCUMENTS

| 629,658 A | 7/1899 | Cargill |
|---|---|---|
| 2,217,783 A | 10/1940 | Bell |

(Continued)

FOREIGN PATENT DOCUMENTS

| CN | 106456991 | 2/2017 |
|---|---|---|
| CN | 108325093 | 7/2018 |

(Continued)

OTHER PUBLICATIONS

"International Application Serial No. PCT/EP2020/086650, International Search Report dated Jun. 24, 2021", (Jun. 24, 2021), 6 pgs.

(Continued)

*Primary Examiner* — Irakli Kiknadze
(74) *Attorney, Agent, or Firm* — Schwegman Lundberg & Woessner, P.A.

(57) ABSTRACT

The present application relates to a radiotherapy apparatus for delivering radiation to a subject. The apparatus comprises a source of radiation configured to rotate about an isocenter and emit radiation in a radiation plane containing said isocentre. The apparatus also comprises a subject support surface configured such that a portion of the subject support surface can be located substantially at the isocenter. The apparatus also comprises a subject support surface rotation mechanism configured to rotate the subject support surface about an axis of rotation that passes through the isocenter, wherein the subject support surface rotation mechanism is located outside the radiation plane.

17 Claims, 11 Drawing Sheets

(58) Field of Classification Search
CPC .......... A61N 5/1039; A61N 2005/1057; A61N 2005/1074; A61N 5/1082; A61N 5/1067; A61N 5/01; A61N 2005/1055; A61N 2005/1059; A61N 2005/1052; A61N 5/107; A61N 2005/105; A61N 2005/1051; A61N 2005/1063; A61B 6/032; A61B 6/0407; A61B 6/5276; A61B 6/488; A61B 6/0492; A61B 6/563; A61B 6/566; A61B 6/542; A61B 6/4085; A61B 6/583; A61B 5/0555; A61B 6/0421; A61B 6/0485; A61B 5/4528; A61B 6/548; A61B 5/702; A61B 5/704; A61B 5/055; A61B 90/16; A61B 34/20; A61B 90/10; A61B 90/14; A61B 6/5247; A61B 2034/2055; A61B 2034/2068; A61B 2090/364; A61B 5/1127; A61B 90/20; A61B 2034/2072; A61B 2034/102; A61B 2090/3983; A61B 2090/3966; A61B 2034/2065; A61B 2090/378; A61B 2090/363; A61B 2090/3937; A61B 2090/371; A61B 6/08; A61B 2090/502; A61B 2090/395; A61B 6/461; A61B 6/467; A61B 6/464; A61B 6/0487; A61B 6/035; A61B 6/4476; G01R 33/20; A47C 31/12; G01T 1/00; A61G 13/12; A61G 13/121; A61G 13/1225; A61G 13/1235; A61G 13/124; A61G 13/1245; A61G 13/125; A61G 13/1255; A61G 2200/54; G06T 7/73; G06T 2207/10081; G06T 2207/30204
USPC ...................................................... 378/65, 68
See application file for complete search history.

(56) References Cited

U.S. PATENT DOCUMENTS

| | | | |
|---|---|---|---|
| 3,259,921 A | 7/1966 | Alsobrook | |
| 3,885,556 A | 5/1975 | Agatani | |
| 3,991,428 A | 11/1976 | Hanson | |
| 4,195,829 A | 4/1980 | Reser | |
| 4,356,577 A | 11/1982 | Taylor et al. | |
| 4,613,122 A | 9/1986 | Manabe | |
| 4,618,133 A | 10/1986 | Siczek | |
| 4,715,073 A | 12/1987 | Butler | |
| 4,856,129 A | 8/1989 | Butler | |
| 5,199,123 A | 4/1993 | Jacques et al. | |
| 5,208,928 A | 5/1993 | Kuck et al. | |
| 5,237,600 A | 8/1993 | Kamata | |
| 5,402,544 A | 4/1995 | Crawford et al. | |
| 5,490,297 A | 2/1996 | Bradcovich et al. | |
| 5,525,905 A * | 6/1996 | Mohapatra | A61B 6/0487 324/318 |
| 5,596,779 A | 1/1997 | Meek | |
| 5,615,430 A * | 4/1997 | Nambu | A61N 5/1049 5/601 |
| 5,619,763 A | 4/1997 | Randolph et al. | |
| 5,802,639 A | 9/1998 | Raasch et al. | |
| 5,903,940 A | 5/1999 | Volker et al. | |
| 5,937,459 A | 8/1999 | Binaghi et al. | |
| 5,940,911 A | 8/1999 | Wang | |
| 6,094,760 A | 8/2000 | Nonaka et al. | |
| 6,240,582 B1 | 6/2001 | Reinke | |
| 6,405,072 B1 * | 6/2002 | Cosman | A61B 90/16 606/130 |
| 6,615,429 B2 | 9/2003 | Weil et al. | |
| 6,640,363 B1 | 11/2003 | Pattee et al. | |
| 6,678,907 B1 | 1/2004 | Voelker et al. | |
| 6,681,423 B2 | 1/2004 | Zachrisson | |
| 6,772,462 B1 | 8/2004 | Harrell | |
| 6,957,456 B2 | 10/2005 | Darling et al. | |
| 8,056,163 B2 | 11/2011 | Lemire et al. | |
| 8,096,007 B2 | 1/2012 | Dyreby et al. | |
| 9,113,804 B2 | 8/2015 | Kimishima | |
| 10,695,586 B2 | 6/2020 | Harper et al. | |
| 12,285,634 B2 | 4/2025 | Eldered et al. | |
| 2002/0077525 A1 | 6/2002 | Costanzo | |
| 2003/0146425 A1 | 8/2003 | Drake et al. | |
| 2004/0098804 A1 | 5/2004 | Varadharajulu et al. | |
| 2004/0261176 A1 | 12/2004 | Plannerer | |
| 2005/0223491 A1 | 10/2005 | McCrimmon | |
| 2006/0193443 A1 | 8/2006 | Reger | |
| 2007/0023066 A1 | 2/2007 | Yokokawa et al. | |
| 2007/0226906 A1 | 10/2007 | Farooqui | |
| 2007/0230660 A1 | 10/2007 | Herrmann | |
| 2008/0086816 A1 | 4/2008 | Farooqui | |
| 2010/0104159 A1 * | 4/2010 | Hirokawa | A61B 6/542 382/131 |
| 2010/0199433 A1 | 8/2010 | Clenet | |
| 2010/0280549 A1 | 11/2010 | Yen | |
| 2011/0199085 A1 | 8/2011 | Allen et al. | |
| 2011/0209286 A1 | 9/2011 | Dane | |
| 2011/0211665 A1 | 9/2011 | Maurer, Jr. et al. | |
| 2011/0313228 A1 | 12/2011 | Handa et al. | |
| 2012/0150018 A1 | 6/2012 | Yamaya et al. | |
| 2013/0111668 A1 | 5/2013 | Wiggers et al. | |
| 2013/0158382 A1 | 6/2013 | Chao | |
| 2013/0227787 A1 | 9/2013 | Herbst et al. | |
| 2013/0259209 A1 | 10/2013 | Goto et al. | |
| 2014/0171725 A1 | 6/2014 | Adler et al. | |
| 2014/0275697 A1 | 9/2014 | Filiberti | |
| 2015/0190295 A1 | 7/2015 | Tso et al. | |
| 2015/0285430 A1 | 10/2015 | Wang | |
| 2015/0352373 A1 | 12/2015 | Subrahmanyam et al. | |
| 2016/0000620 A1 | 1/2016 | Koch | |
| 2016/0095558 A1 | 4/2016 | Choy et al. | |
| 2016/0331613 A1 | 11/2016 | Lee et al. | |
| 2017/0095219 A1 | 4/2017 | Wakahara | |
| 2017/0258414 A1 | 9/2017 | Guertin et al. | |
| 2017/0319410 A1 | 11/2017 | Lee | |
| 2017/0340903 A1 | 11/2017 | Ie et al. | |
| 2018/0078223 A1 | 3/2018 | Oishi | |
| 2018/0085603 A1 | 3/2018 | Kruesi et al. | |
| 2018/0133518 A1 | 5/2018 | Harper et al. | |
| 2018/0147105 A1 | 5/2018 | Timm et al. | |
| 2018/0154183 A1 | 6/2018 | Sahadevan | |
| 2018/0280733 A1 | 10/2018 | Weidlich et al. | |
| 2018/0339172 A1 | 11/2018 | Stahl et al. | |
| 2019/0368652 A1 | 12/2019 | Olea | |
| 2020/0043624 A1 | 2/2020 | Schnarr et al. | |
| 2020/0289353 A1 | 9/2020 | Scherff | |
| 2020/0390246 A1 | 12/2020 | Chen et al. | |
| 2021/0031055 A1 | 2/2021 | Jiang et al. | |
| 2021/0100366 A1 | 4/2021 | Liu | |
| 2021/0186789 A1 | 6/2021 | Campbell et al. | |
| 2022/0339469 A1 | 10/2022 | Eldered et al. | |
| 2023/0025744 A1 | 1/2023 | Feng et al. | |
| 2023/0028350 A1 | 1/2023 | Carlander et al. | |
| 2023/0111290 A1 | 4/2023 | Wiberg | |

FOREIGN PATENT DOCUMENTS

| | | |
|---|---|---|
| EP | 4076645 | 10/2022 |
| JP | 06224 A | 1/1994 |
| JP | 10127793 | 5/1998 |
| JP | 2002325854 A | 11/2002 |
| WO | 0232312 | 4/2002 |
| WO | 2007018646 | 2/2007 |
| WO | WO-2007127970 A2 | 11/2007 |
| WO | 2011088399 | 7/2011 |
| WO | 2018093937 | 5/2018 |

OTHER PUBLICATIONS

"International Application Serial No. PCT/EP2020/086650, Written Opinion dated Jun. 24, 2021", (Jun. 24, 2021), 8 pgs.
"United Kingdom Application Serial No. 1918753.3, Examination Report dated Dec. 9, 2020" (Dec. 9, 2020), 3 pgs.
"International Application Serial No. PCT EP2020 086663, International Search Report dated Apr. 14, 2021", (Apr. 14, 2021), 3 pgs.

(56) References Cited

OTHER PUBLICATIONS

"International Application Serial No. PCT EP2020 086663, Written Opinion dated Apr. 14, 2021", (Apr. 14, 2021), 5 pgs.
"United Kingdom Application Serial No. 1918757.4, Examination Report dated Jun. 17, 2020", (Jun. 17, 2020), 7 pgs.
"European Application Serial No. 1918757.4, European Search Report dated Jun. 17, 2020", (Jun. 17, 2020), 7 pgs.
"International Application Serial No. PCT EP2020 087307, International Search Report dated Apr. 26, 2021", (Apr. 26, 2021), 3 pgs.
"International Application Serial No. PCT EP2020 087307, Written Opinion dated Apr. 26, 2021", (Apr. 26, 2021), 6 pgs.
"International Application Serial No. PCT CN2020 131937, International Search Report dated Mar. 1, 2021", (Mar. 1, 2021), 4 pgs.
"International Application Serial No. PCT CN2020 131937, Written Opinion dated Mar. 1, 2021", (Mar. 1, 2021), 6 pgs.
"United Kingdom GB1918757.4, Examination Report under Section 18(3) mailed Dec. 22, 2022", (Dec. 22, 2022), 4 pgs.
"U.S. Appl. No. No. 17/757,678 Preliminary Amendment Filed with Application", 10 pgs.
"U.S. Appl. No. 17/757,682 Preliminary Amendment Filed with Application", 8 pgs.
"United Kingdom Application Serial No. 1918753.3, Examination Report mailed Aug. 23, 2022", 1 pg.
U.S. Appl. No. 17/757,675, filed Jun. 17, 2022, Radiotherapy Apparatus for Delivering Radiation to a Subject.
U.S. Appl. No. 17/757,678, filed Jun. 17, 2022, Patient Support Apparatus.
U.S. Appl. No. 17/757,682, filed Jun. 17, 2022, Beam Stopper for a Radiotherapy Device.
"U.S. Appl. No. 17/757,682, Non Final Office Action mailed Jun. 21, 2024", 15 pgs.
"European Application Serial No. 20902566.7, European Search Report dated Jan. 5, 2024", (Jan. 5, 2024), 7 pgs.
"U.S. Appl. No. 17/757,675, Non Final Office Action mailed Jul. 18, 2024", 10 pgs.
"U.S. Appl. No. 17/757,682, Response filed Sep. 20, 2024 to Non Final Office Action mailed Jun. 21, 2024", 13 pgs.
"U.S. Appl. No. 17/757,682, Final Office Action mailed Oct. 15, 2024", 13 pgs.
"U.S. Appl. No. 17/757,675, Response filed Nov. 18, 2024 to Non Final Office Action mailed Jul. 18, 2024", 11 pgs.
"U.S. Appl. No. 17/757,678, Restriction Requirement mailed Nov. 25, 2024", 7 pgs.
"U.S. Appl. No. 17/757,682, Response filed Dec. 16, 2024 to Final Office Action mailed Oct. 15, 2024", 11 pgs.
"U.S. Appl. No. 17/757,675, Notice of Allowance mailed Dec. 18, 2024", 7 pgs.
"U.S. Appl. No. 17/757,675, Supplemental Notice of Allowability mailed Jan. 3, 2025", 3 pgs.
"U.S. Appl. No. 17/757,682, Advisory Action mailed Jan. 21 2025", 3 pgs.
"U.S. Appl. No. 17/757,678, Response filed Jan. 27, 2025 to Restriction Requirement mailed Nov. 25, 2024", 11 pgs.
"U.S. Appl. No. 17/757,682, Response filed Feb. 28, 2025 to Advisory Action mailed Jan. 21, 2025", 11 pages.
"U.S. Appl. No. 17/757,682, Notice of Allowance mailed Mar. 12, 2025", 12 pgs.
"U.S. Appl. No. 17/757,678, Non Final Office Action mailed Apr. 22, 2025", 24 pgs.

* cited by examiner

RADIOTHERAPY APPARATUS FOR DELIVERING RADIATION TO A SUBJECT

PRIORITY APPLICATIONS

This application is a U.S. National Stage Filing under 35 U.S.C. § 371 from International Application No. PCT/EP2020/086650, filed on Dec. 17, 2020, and published as WO2021/122899 on Jun. 24, 2021, which claims the benefit of priority to United Kingdom Application No. 1918753.3, filed on Dec. 18, 2019; the benefit of priority of each of which is hereby claimed herein, and which applications and publication are hereby incorporated herein by reference in their entireties.

This disclosure relates generally to a radiotherapy apparatus, and in particular to positioning a subject during the delivery or application of radiotherapy.

BACKGROUND

Radiotherapy uses ionising radiation to treat a human or animal body. In particular, radiotherapy is commonly used to treat tumours within the human or animal body. In such treatments, cells forming part of the tumour are irradiated by ionising radiation in order to destroy or damage them. However, in order to apply a prescribed dose of ionising radiation to a target location or target region, such as a tumour, the ionising radiation will typically also pass through healthy tissue of the human or animal body. Therefore, radiotherapy has the desirable consequence of irradiating and damaging a target region, but can also have the undesirable consequence of irradiating and damaging healthy tissue. In radiotherapy treatment, it is desirable to align the dose received by the target region with a prescribed dose and to minimise the dose received by healthy tissue.

Modern radiotherapy treatment uses techniques to reduce the radiation dose to healthy tissue and thereby provide a safe treatment. For example, one approach to minimising a radiation dose received by healthy tissue surrounding a target region is to direct the radiation towards the target region from a plurality of different angles, for example by rotating a source of radiation around the patient by use of a rotating gantry. In this case, the angles at which radiation is applied are selected such that each beam of radiation passes through the target region. In this way, a cumulative radiation dose may be built up at the target region over the course of a treatment arc in which the radiation source rotates through a certain angle. Radiation is emitted in a radiation plane which is co-incident with the plane of the gantry around which the radiation source rotates and radiation may thus be delivered to a radiation isocentre at the centre of the gantry regardless of the angle to which the radiation head is rotated around the gantry. Because the radiation is applied from a plurality of different angles, the same, high, cumulative radiation dose is not built up in the healthy tissue since the specific healthy tissue the radiation passes through varies with angle. Therefore, a unit volume of the healthy tissue receives a reduced radiation dose relative to a unit volume of the target region. Treatments that utilise rotation of the gantry in this manner are known as coplanar. However, after the radiation source has been rotated 180°, it will be appreciated that any subsequent radiation beams begin to pass through regions of healthy tissue which have already been irradiated. This increases the radiation dose applied to healthy tissue. Accordingly, when using such a method the volume of healthy tissue available to spread the radiation dose is relatively small, thus imposing restrictions on the treatment which can be provided by such devices.

Therefore, an alternative approach to minimising the radiation dose received by healthy tissue surrounding a target region is to rotate the patient relative to the plane of radiation. As the angle of the patient varies relative to the plane of the gantry, so does the healthy tissue the radiation passes through. In order to further reduce the radiation dose relative to a unit volume of the target region, it is desirable to provide a treatment that combines both of these rotations. An example of a known device that combines the rotation of the patient with the rotation of the radiation source is shown in FIG. 1. This shows that the patient 140, who is supported on the subject support surface 114, which is also referred to herein as a patient support surface 114, can be rotated whilst the gantry 116 may also rotate about the patient support surface 114. The gantry 116 shown in FIG. 1 is a C-arm gantry or open gantry. The rotation mechanism 117 rotates the gantry 116 about a fixed axis 119. As the gantry 116 is rotated, radiation emitted by a radiation source 106 can sweep out a circle. Radiation can be applied to the patient 140 from a plurality of angles around the circle. The circle may be described as lying in a radiation plane. The radiation axis lies in the radiation plane. The radiation axis makes an angle of 90° with respect to the fixed axis 119.

The rotation mechanism 120 for the patient support surface 114 is located underneath the gantry 116 of the radiotherapy device, while a rotation mechanism for the gantry 116 is located opposite the patient support surface 114. The rotation mechanism 120 for the patient support surface 114 is located underneath the gantry 116 so that the axis of rotation of the patient support surface 111 will be in the radiation plane. In particular, the axis of rotation of the patient support surface 111 passes through the isocenter 124 of the radiotherapy device, so that the patient support surface 114 is rotated about the isocenter 124. When the patient support surface 114 is in its neural position, the axis of rotation of the patient support surface 111 is substantially vertical (perpendicular to the plane of the floor) and this can also be called a vertical axis 111. The longitudinal axis 113 is parallel to long side of the patient support surface 114 in its neutral position and the transverse axis 115 is parallel to the short end of the patient support surface 114 in its neutral position. The rotation mechanism 120 is located within the plane of radiation. Treatments utilising both the rotation of the radiation and the patient 140 are known as non-coplanar treatments.

Some recently developed radiotherapy devices comprise ring-based gantries (or bores), such as that shown in FIG. 2. Typically, the bore of a radiotherapy device is cylindrical. A patient support surface 114 is positioned in the bore such that radiation can be directed toward a patient 140 positioned on the support surface 114. The bore of the apparatus can be formed by a framework, which may otherwise be described as a chassis, a shielding structure, a shell, or a casing. The framework defines the outer surface of the device which the patient 140 sees upon entering the treatment room, as well as defining the inner surface of the bore which the patient 140 sees when positioned inside the bore. The framework also defines a hollow region of annular cross-section in which the gantry 116 can be both rotated and tilted. Thus, the patient 140 is shielded from the rotatable gantry 116. Movement of the gantry 116 is hidden from the patient's view, reducing intimidation and distress which may otherwise be caused if the patient 140 were able to see rotation of the large gantry 116, as they would for an open gantry as shown in FIG. 1, and also reducing the likelihood that the patient can accidentally touch or otherwise interfere with the movement of the gantry 116. This means that the gantry 116 can be rotated quickly, efficiently and safely. Ring-based gantries are also desirable because they increase device stability. The ring-based gantry is supported by the floor and rests upon it. However, the geometry of a ring-based gantry and its connection to the floor makes it impossible to rotate the patient support surface 114 about the isocenter 124.

Another problem that arises when attempting to minimise the radiation dose received by healthy tissue surrounding a target region can be found in accurately locating the position of the target region relative to the device. For example, movement of the patient can cause movement of unhealthy tissue such as a tumour and thus the dose applied to the target region may be decreased and the dose applied to the healthy tissue may be increased. In other words, if a patient moves during or prior to radiotherapy treatment, this can cause a high cumulative dose to build up in a region of healthy tissue instead of in a target region. This can reduce the effectiveness of the radiotherapy for treating the target region and can cause damage to otherwise healthy tissue.

This problem is also caused by flexing of the table top of the patient support surface when the table top is extended into the device. In normal operation, the table top will initially be positioned substantially outside the plane of the gantry to enable the patient to easily position themselves onto the table. The table top will then be extended into the plane of the gantry and, in particular, such that that the target region is aligned with the isocenter of the device. In the extended position, the table top will flex with a magnitude dependent on the position of the table top, the position of the patient on the table top and the weight of the patient. Due to the table top flex, the target region will move relative to the isocenter and this will result in healthy tissue receiving a higher dose of radiation than is necessary. Furthermore, during spiral treatments, which are used to target a larger target region, the table top is moved during the treatment. Spiral treatments involve the patient being moved, by movement of a table top, whilst the radiation source moves around the gantry and emits radiation. Accordingly, the amount of table top flex will vary during the treatment and so the position of the target region relative to the isocenter will vary during the treatment, resulting in healthy tissue receiving a higher dose of radiation than is necessary. This problem occurs for all radiotherapy devices with an extendable table top. However, this problem is particularly significant for radiotherapy devices with a bore solution, because these devices will often have a longer top extension. The longer the table top extension, the more table top flex will occur and the greater will be the change in position of the target region.

Previous solutions to this problem involve manually positioning the patient, for example with the assistance of lasers. However, particularly for automatic and spiral treatments this does not work without repeatedly stopping the treatment and thereby resulting in longer treatment times and lower efficiency. It is possible to detect the position of the target region by taking an image, however doing so is harmful to the patient. It would be desirable to know the position of the treatment region as accurately as possible at all times during the treatment without the need to take additional images. Accurately knowing the position of the target region allows the radiation to be focused where it is needed, ideally within 1 mm of the target region, thereby minimising the radiation dose received by the healthy tissue surrounding the target region.

SUMMARY

An invention is set out in the claims.

FIGURES

Specific embodiments are now described, by way of example only, with reference to the drawings, in which.

OVERVIEW

Figure 1:
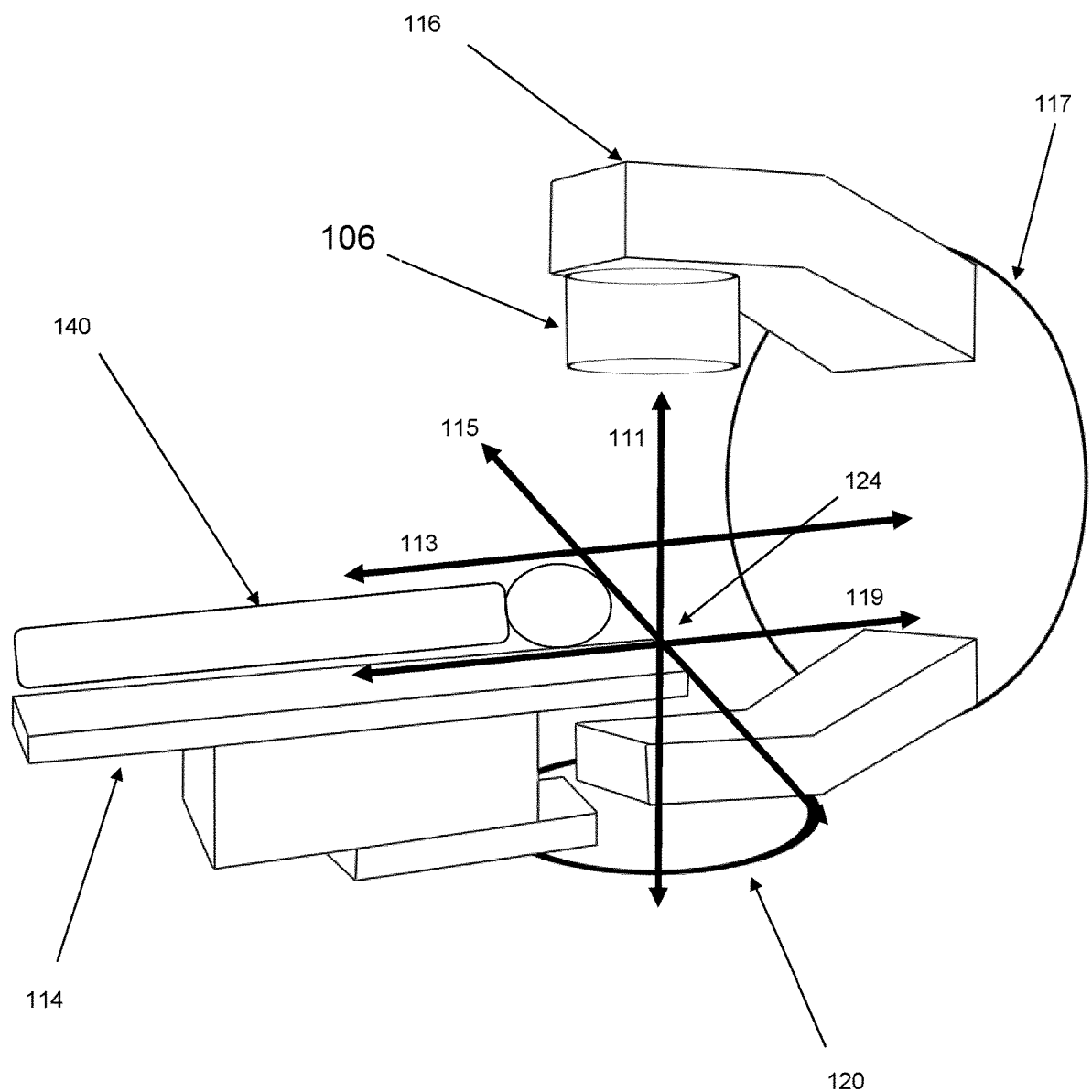
FIG. 1 depicts a known radiotherapy apparatus with rotation means located within the plane of the radiation.
Figure 2:
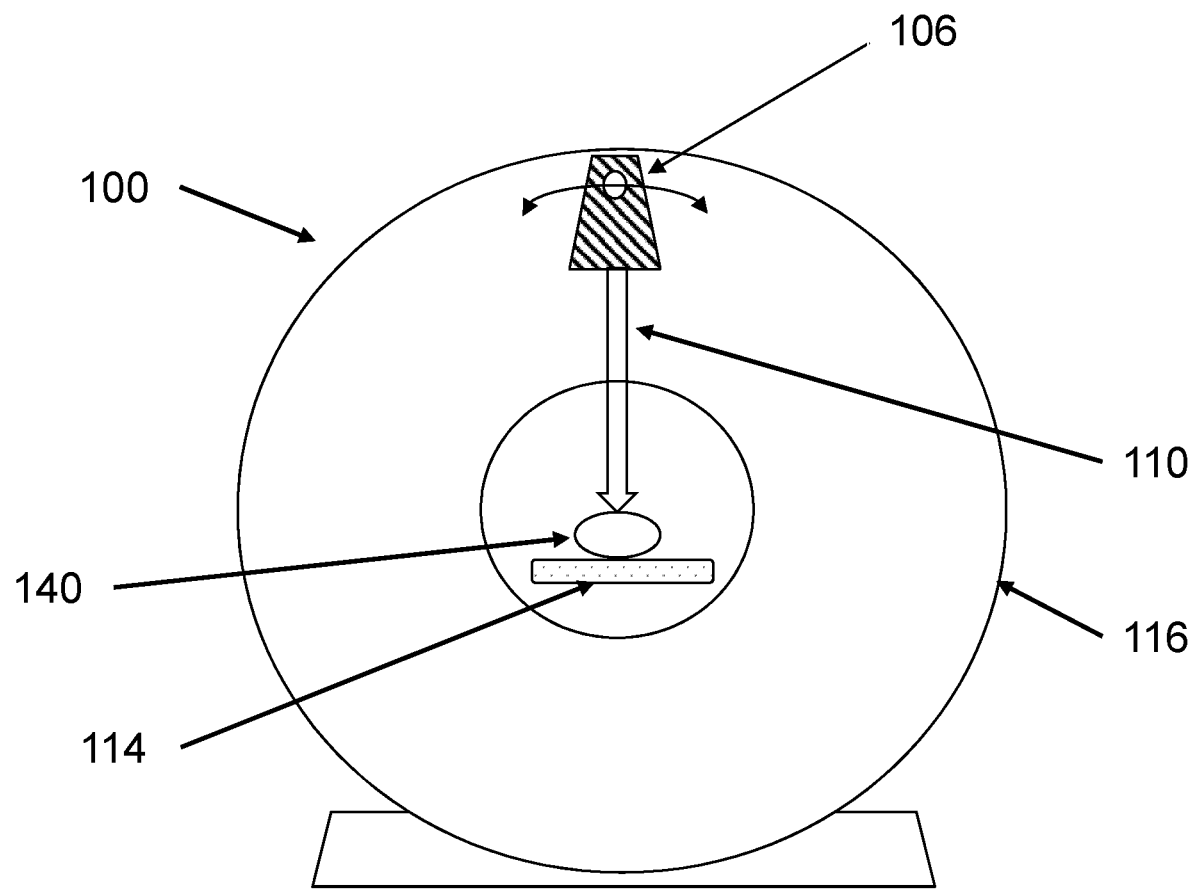
FIG. 2 depicts a front view of a radiotherapy device.

By providing a radiotherapy apparatus for delivering radiation to a subject, with the apparatus comprising a subject support surface configured such that a portion of the subject support surface can be located substantially at the isocenter and a subject support surface rotation mechanism configured to rotate the subject support surface about an axis of rotation that passes through the isocenter, wherein the subject support surface rotation mechanism is located outside the radiation plane, a number of benefits are provided. The apparatus provides means for allowing the dose received by healthy tissue during a radiotherapy treatment to be minimised. By rotating the subject support surface, for example with a patient positioned on it, it is possible to spread the radiation through the healthy tissue while rotating about the isocenter ensures that the maximum amount of radiation still passes through the target region which maximises the efficiency of the treatment and allows the treatment time to be reduced. However, if in order to rotate a couch about the isocenter, the rotation mechanism is located within the plane of the radiation, then it is not possible to use the couch and rotation mechanism in radiotherapy device using a bore because the gantry and the rotation mechanism would obstruct one another. Locating the subject support surface rotation mechanism outside the radiation plane allows the dose received by healthy tissue of the subject during the radiotherapy treatment to be minimised for a wide range of radiotherapy apparatuses with different geometries. For example, these benefits can be achieved in radiotherapy apparatuses that comprise a bore for receiving the subject.

By providing a system for positioning a subject in a radiotherapy apparatus, with the system comprising a subject support surface with an extendable table top and one or more sensors that are configured to measure a vertical position of the extendable table top, as well as a processor configured to determine a deflection of the extendable table top using the measured position and control a treatment of the radiotherapy apparatus according to the deflection, a number of benefits are provided. Using this system to determine a deflection profile allows treatments, such as spiral treatments for example, to be performed accurately without the need for re-imaging the patient during treatment. This reduces the amount of imaging radiation that the patient is exposed to which reduces the harm done to a patient. Removing the requirement for re-imaging increases the speed at which a treatment can be performed, thereby increasing patient throughput and improving the efficiency of the radiotherapy apparatus. The system also enables the position of the target region to be known with greater certainty and accuracy, which enables the treatment to be performed with greater accuracy and confidence in treating the target region. This also minimises the radiation received by healthy tissue.

DETAILED DESCRIPTION

When administering a treatment to a subject or patient 140 with a radiotherapy apparatus comprising a source of radiation 106 configured to rotate about an isocenter 124 and emit radiation in a radiation plane containing said isocentre 124, rotating the subject about the isocenter 124 allows the dose received by healthy tissue during the radiotherapy treatment to be minimised. This can be achieved by providing a subject support surface rotation mechanism 120 connected to the subject support surface 114 and configured to rotate the subject support surface about the isocenter 124. Rotating the subject support surface 114 about an axis of rotation that passes through the isocenter 124 ensures that the radiation will pass through the same point, regardless of the rotation angle of the subject support surface 114. This is advantageous because, for example, by locating a target region of a patient 140 at the isocenter 124, it is possible to ensure that the radiation passes through the target region for all rotation angles of the subject support surface 114. By rotating the subject support surface 140 (and therefore a patient 140), it is possible to spread the radiation through the healthy tissue while rotating about the isocenter 124 ensures that the maximum amount of radiation still passes through the target region which maximises the efficiency of the treatment and allows the treatment time to be reduced. Locating the subject support surface rotation mechanism 120 outside the radiation plane allows the dose received by healthy tissue of the subject 140 during the radiotherapy treatment to be minimised for a wide range of radiotherapy apparatuses with different geometries. In particular, radiotherapy apparatuses that comprise a bore for receiving the subject 140. By way of background, in known devices the rotation mechanism is located within the plane of radiation, as shown in FIG. 1, which make them unsuitable for radiotherapy apparatuses that comprise a bore.

Figure 3:
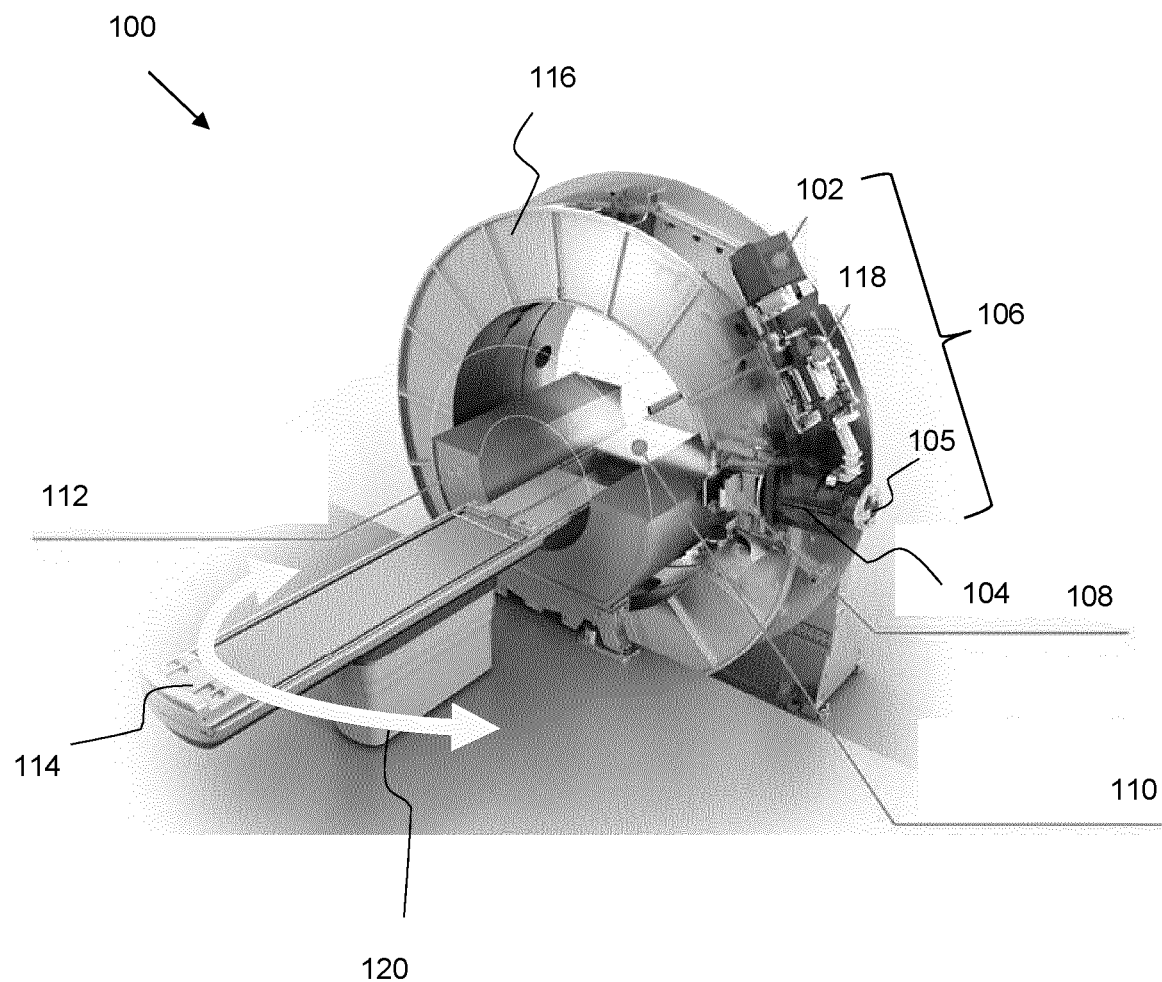
FIG. 3 depicts an isometric view of an embodiment of the radiotherapy device.

In accordance with one embodiment, FIG. 3 depicts a radiotherapy device suitable for delivering a beam of radiation to a patient during radiotherapy treatment. The device and its constituent components will be described generally for the purpose of providing useful accompanying information for the present invention. The device depicted in FIG. 3 is in accordance with the present disclosure and is suitable for use with the disclosed systems and apparatuses, although not all of the features are necessarily present, or as depicted in FIG. 3. While the device in FIG. 3 is an MR-linac, the implementations of the present disclosure may be any radiotherapy device, for example a linac device. FIG. 3 shares features common with known devices such as Versa HD™ in particular, the features involved in producing the treatment beam 110. The embodiment shown in FIG. 3 is modified over known devices in accordance with the invention by the provision of a subject support surface rotation mechanism 120, as will be described in more detail below.

The device depicted in FIG. 3 is an MR-linac. The device comprises both MR imaging apparatus 112 and radiotherapy (RT) apparatus which may comprise a linac device. In operation, the MR scanner produces MR images of the patient 140, which can be used to determine the position of the patient 140 on the couch 114 and also the position of a target region, such as a tumour, within the patient 140 so that a target region's position relative to the couch 114 may be determined. The linac device produces and shapes a beam of radiation and directs it toward a target region within a patient's body in accordance with a radiotherapy treatment plan. The usual 'housing' which would cover the MR imaging apparatus 112 and RT apparatus in a commercial setting such as a hospital is not depicted in FIG. 3.

The MR-linac device depicted in FIG. 3 comprises a source of radiation 106. The source of radiation 106 may comprise beam generation equipment, such as one or more of: a source of radiofrequency waves 102, a circulator 118, a source of electrons 105, a waveguide 104, and a target (not shown). The MR-linac may also comprise a collimator 108 such as a multi-leaf collimator configured to collimate and shape the beam, MR imaging apparatus 112, and a patient support surface 114. The device also comprises a housing which, together with the ring-shaped gantry defines a bore. The movable subject support surface 114 can be used to move a patient, or other subject, into the bore when an MR scan and/or when radiotherapy is to commence or during treatment. The MR imaging apparatus 112, RT apparatus, and a subject support surface actuator are communicatively coupled to a controller or processor. The controller is also communicatively coupled to a memory device comprising computer-executable instructions which may be executed by the controller.

The RT apparatus comprises a source of radiation 106 and a radiation detector (not shown). Typically, the radiation detector is positioned diametrically opposed to the radiation source 106. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

The radiation source 106 defines the point at which the treatment beam 110 is introduced into the bore. The radiation source 106 may comprise a beam generation system, which may comprise a source of RF energy 102, an electron gun 105, and a waveguide 104. The beam generation system is attached to the rotatable gantry 116 so as to rotate with the gantry 116. In this way, the radiation source 106 is rotatable around the patient 140 so that the treatment beam 110 can be applied from different angles around the gantry 116. In a preferred implementation, the gantry 116 is continuously rotatable. In other words, the gantry 116 can be rotated by 360 degrees around the patient, and in fact can continue to be rotated past 360 degrees. The gantry 116 rotates about a mechanical isocenter, which is the point in space about which the gantry 116 rotates and about a fixed axis 119. The radiation isocenter can be defined as the point where the radiation beams intersect. These two isocenters 124 need not be the same, although they can be. In this disclosure, the term isocenter 124 can refer to either or both of these. The isocenter 124 is located within the radiation plane. The gantry 116 may be ring-shaped. In other words, the gantry 116 may be a ring-gantry with a bore. The gantry 116 may also not be ring-shaped and may instead be an open gantry such as that shown in FIG. 1.

The source 102 of radiofrequency waves, such as a magnetron, is configured to produce radiofrequency waves. The source 102 of radiofrequency waves is coupled to the waveguide 104 via circulator 118, and is configured to pulse radiofrequency waves into the waveguide 104. Radiofrequency waves may pass from the source 102 of radiofrequency waves through an RF input window and into an RF input connecting pipe or tube. A source of electrons 105, such as an electron gun, is also coupled to the waveguide 104 and is configured to inject electrons into the waveguide 104. In the source of electrons, electrons are thermionically emitted from a cathode filament as the filament is heated. The temperature of the filament controls the number of electrons injected. The injection of electrons into the waveguide 104 is synchronised with the pumping of the radiofrequency waves into the waveguide 104. The design and operation of the radiofrequency wave source 102, electron source and the waveguide 104 is such that the radiofrequency waves accelerate the electrons to very high energies as the electrons propagate through the waveguide 104.

The source of radiation 106 is configured to direct a beam 110 of therapeutic radiation toward a patient positioned on the patient support surface 114. The source of radiation 106 may comprise a heavy metal target toward which the high energy electrons exiting the waveguide are directed. When the electrons strike the target, X-rays are produced in a variety of directions. A primary collimator may block X-rays traveling in certain directions and pass only forward traveling X-rays to produce a treatment beam 110. The X-rays may be filtered and may pass through one or more ion chambers for dose measuring. The beam can be shaped in various ways by beam-shaping apparatus, for example by using a multi-leaf collimator 108, before it passes into the patient as part of radiotherapy treatment.

In some implementations, the source of radiation 106 is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window is substantially transparent to electrons and allows electrons to exit the flight tube.

The radiotherapy apparatus/device depicted in FIG. 3 also comprises MR imaging apparatus 112. The MR imaging apparatus 112 is configured to obtain images of a subject positioned, i.e. located, on the subject support surface 114. The MR imaging apparatus 112 may also be referred to as the MR imager. The MR imaging apparatus 112 may be a conventional MR imaging apparatus 110 operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by the controller.

The controller is a computer, processor, or other processing apparatus. The controller may be formed by several discrete processors; for example, the controller may comprise an MR imaging apparatus processor, which controls the MR imaging apparatus 112; an RT apparatus processor, which controls the operation of the RT apparatus; and a subject support surface processor which controls the operation and actuation of the subject support surface. The controller is communicatively coupled to a memory, i.e. a computer readable medium.

The linac device also comprises several other components and systems as will be understood by the skilled person. For example, in order to ensure the linac does not leak radiation, appropriate shielding is also provided.

The patient support surface 114 may serve to support an object. The object may be a human body (such as a patient), an animal body or a material sample. The subject support surface 114 is configured to move parallel to the longitudinal axis 113 between a first position substantially outside the bore, and a second position substantially inside the bore. In the first position, a patient 140 or subject can mount the subject support surface 114. The subject support surface 114, and patient 140, can then be extended inside the bore, to the second position, in order for the patient 140 to be imaged by the MR imaging apparatus 112 and/or imaged or treated using the RT apparatus. The movement of the subject support surface 114 is effected and controlled by a subject support surface actuator, which may be described as an actuation mechanism. The actuation mechanism is configured to move the subject support surface 114 in a direction parallel to, and defined by, the longitudinal axis of the subject support surface 114. The terms subject and patient are used interchangeably herein such that the subject support surface 114 can also be described as a patient support surface 114. The subject support surface 114 may also be referred to as a movable or adjustable couch or table.

The present invention is distinguished over known devices as follows. The subject support surface 114 is connected to a subject support surface rotation mechanism 120. The rotation mechanism 120 can be attached to the floor as shown or, for example, can be attached to the device housing or gantry 116 (as shown in, for example, FIG. 4A). The rotation mechanism 120 is configured to rotate the patient support surface 114 with the axis of rotation of the patient support surface 114 passing through the isocentre 124 of the gantry 116. The patient support surface 114 or part thereof can be rotated around (or about) the longitudinal axis 113 (roll), around the transverse axis 115 (pitch), or about an axis perpendicular to the floor 111 (yaw), or any combination of these.

Although in FIG. 3 the plane of the rotation of the patient support surface 114 is illustrated as being parallel to the illustrated floor (as is defined by the xy plane, which corresponds to the plane of the patient support surface 114 in its neutral position where x is the longitudinal axis 113 and y is the transverse axis 115), with rotation as yaw about the axis 111, by way of example, the angle of the plane of rotation relative to the floor could be at an angle of 3, 15, 45 or 90 degrees to the floor. However, for reasons of patient comfort, the angle will usually be kept fairly low. It is also possible for the tilt to be changed either prior to, or during, treatment. The subject support surface rotation mechanism is configured to rotate the subject support surface +/−40-20 degrees about the subject support surface axis of rotation, more preferably 35-25 degrees, most preferably 30 degrees. The rotation mechanism 120 and/or the patient support surface 114 may also be connected to an additional rotation mechanism (not shown) configured to rotate the rotation mechanism 120 and/or the patient support surface 114 in a different plane, wherein the axis of rotation also passes through the isocenter 124. In this way, the patient support surface 114 may be connected to more than one rotation mechanism, each configured to move the patient support surface 114 in a different plane. Alternatively, a single rotation mechanism 120 may be configured to rotate the patient support surface 114 in more than one plane with the axis of rotation of each of the rotation planes of the patient support surface 114 passing through the isocenter 124. The primary consideration is that the centre of rotation (about whichever axis) is located at the isocenter 124, or close to the isocenter 124. As a result, the treatment beam can be consistently focused on the area requiring treatment.

By rotating the couch and hence the patient around the isocenter, the radiation dose can be spread through the healthy tissue so that the radiation dose received by healthy tissue surrounding a target region is minimised. This improves patient 140 wellbeing. If the rotation of the couch 114 was not about the isocenter 124, then the location of the target region would move with respect to the isocenter 124 (and focus of the radiation) and, accordingly, this would result in an increased dosage of radiation being received by healthy tissue. Furthermore, this would result in a longer treatment time because the target region would not receive the intended dosage of radiation.

The disclosure provides rotation means for rotating a patient support surface around an isocenter 124, whilst locating the patient support surface rotation mechanisms 120 outside the radiation plane. This is particularly useful for ring gantry/bore solutions or devices with 360° rotation of the gantry 116, for which it is problematic to position the rotation mechanism 120 within the radiation plane without interfering with the gantry 116. However, this disclosure is applicable to any radiotherapy device. Whilst the disclosure is not limited to bore solutions (ring gantries), bore solutions offer improved device stability. Furthermore, bore solutions are less imposing or alarming for patients. Bore solutions therefore may be desirable. The disclosure provides means to supply non-coplanar treatments (in which both gantry 116 and patient support surface 114 are rotated) in a radiotherapy device with a bore solution.

The disclosure provides rotation means which are located outside of the plane of the gantry 116 and therefore the plane of radiation, or isoline. Positioning the rotation means 120 outside the plane of radiation minimises radiation interference.

Examples of specific linkages and structures for rotating a subject support surface about an axis of rotation that passes through the isocenter, wherein the subject support surface rotation mechanism is located outside the radiation plane, will now be described.

Figure 4A:
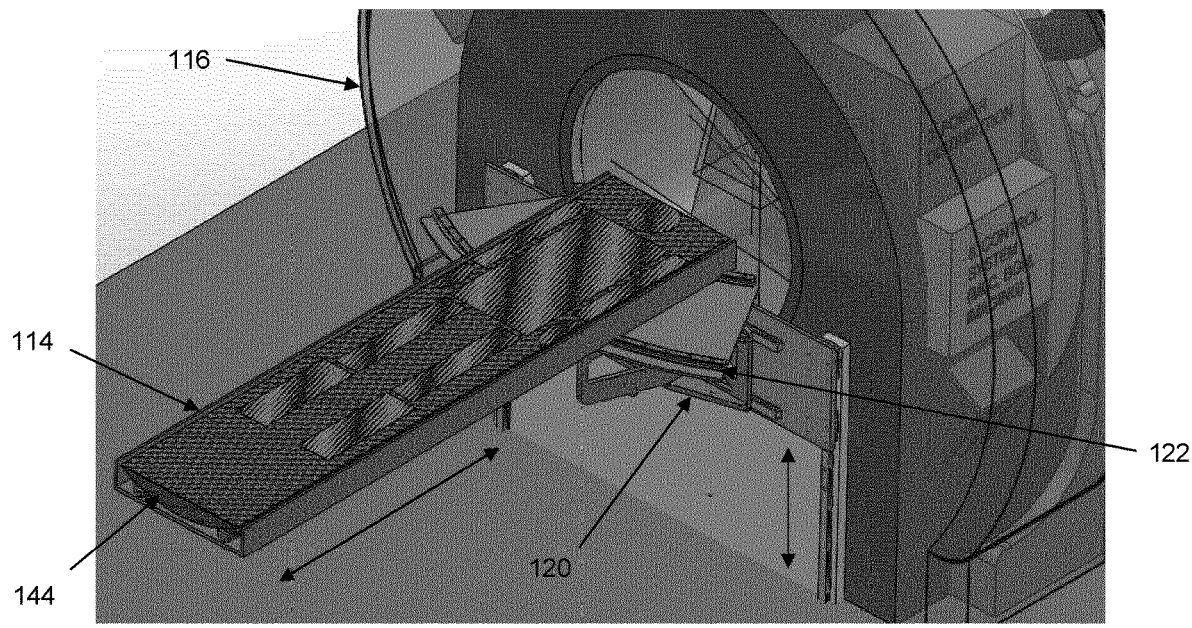
FIG. 4A depicts an isometric view of an embodiment of the radiotherapy device comprising a curved rail.
Figure 4B:
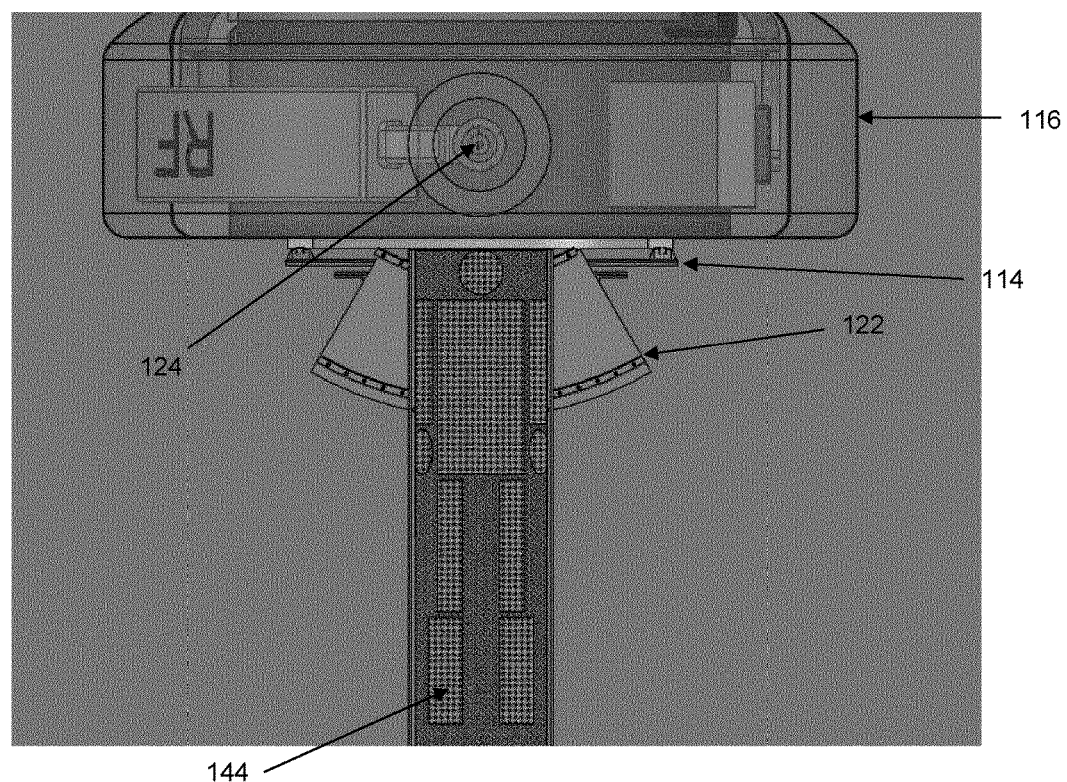
FIG. 4B depicts a plan view of an embodiment of the radiotherapy device comprising a curved rail.
Figure 5:
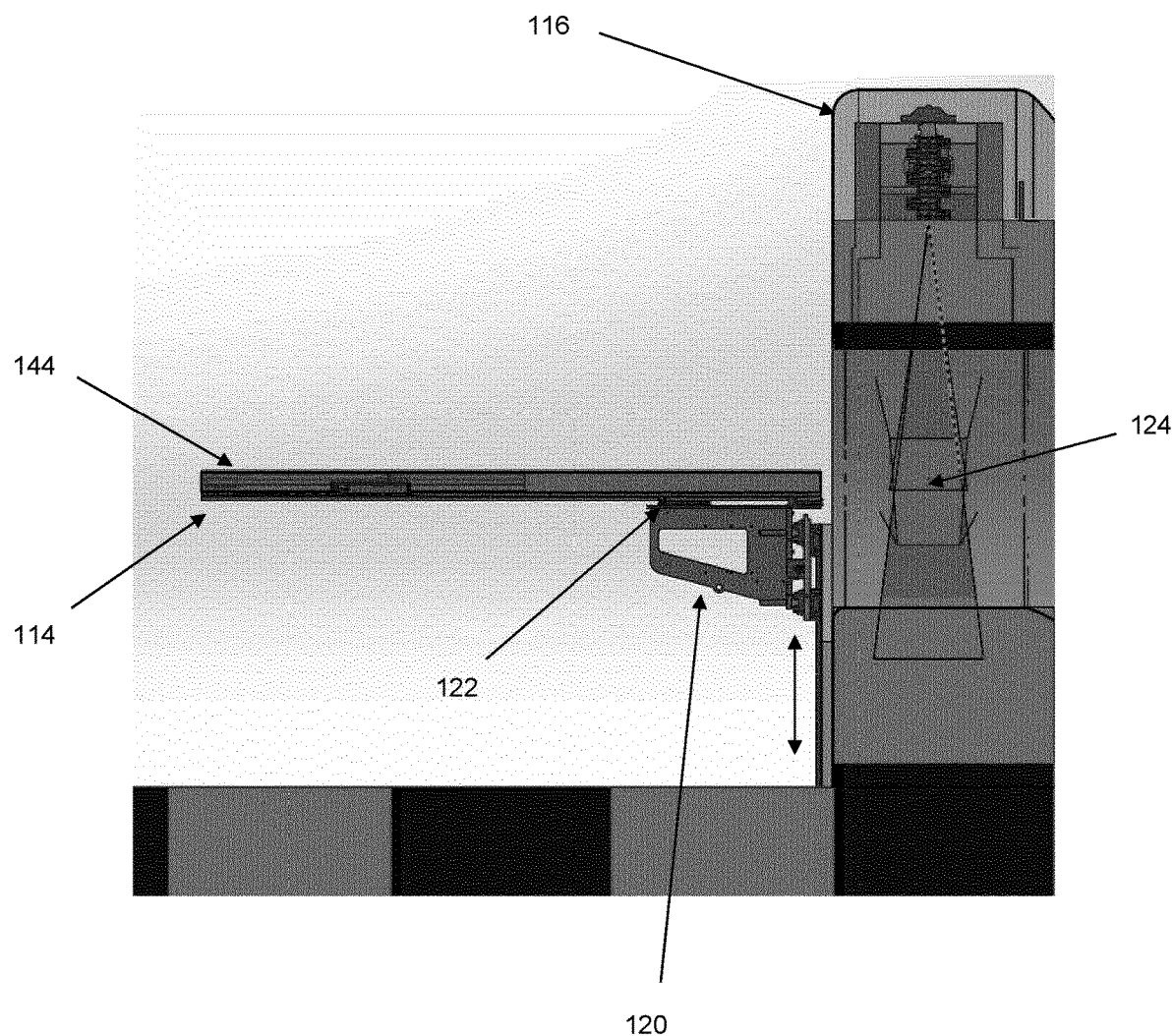
FIG. 5 depicts a side elevation view of an embodiment of the radiotherapy device comprising a curved rail, with an unloaded subject support surface in its non-extended position.

One embodiment is shown from three different perspectives in FIGS. 4A, 4B and 5. These figures show a patient support surface 114 (which may also be described as a couch or patient positioning system) supported by and connected to a rotation mechanism 120. The couch 114 is connected directly to the rotation mechanism 120 or via an intermediary and can be connected by any suitable means, for example, mechanically. The couch 114 may include a number of rollers, a table top 144, a table base, or other parts. In these figures, the rotation mechanism 120 is connected to the gantry 116 but it could be connected to a floor, a wall or other support structure instead or as well. The rotation mechanism 120 shown here makes use of two curved guides or rails 122, with the centre of curvature for both curved guides, which may be curved guide rails 122 being located substantially at the isocenter 124. For example, the center of curvature (and the center of rotation of the patient support surface 114) could be within 0.005 to 0.015 mm, more preferably 0.01 mm, 0.05 mm to 0.15 mm, more preferably 0.1 mm, 0.15 mm to 0.25 mm, more preferably 0.2 mm, 0.25 to 0.35 mm, more preferably 0.3 mm, 0.35 mm to 0.45 mm, more preferably 0.4 mm, 0.45 mm to 0.55 mm, more preferably 0.5 mm, 0.5 mm to 1.5 mm, more preferably 1 mm, or another distance of the isocenter 124. Ideally, the centre of curvature of each curved rails 122 and the center of rotation of the couch 114 will be as close to the isocenter 124 as possible. There could be one curved rail 122 or any larger number. In one example in which there are two curved rails 122, both of the curved rails 122 have the same radius. In another example, the two curved rails 122 have different radii but, the centre of curvature for both of the curved rails 122 is still the same.

The rotation mechanism 120 itself can be moved up and down in any direction, such as vertically as shown in FIG. 4A. The patient support surface 114 can move in any direction. Alternatively, or as well, the patient support surface 114 may comprise a table top 144 which can move independently from the rest of the patient support surface 114, such as a table base, and in any direction, for example, a longitudinal direction (along a longitudinal axis 113 of the patient support surface 114), a lateral direction (along a transverse axis 113 of the patient support surface 114), a vertical direction (along a vertical axis 111 that is an axis perpendicular to the floor), or a direction oblique to any of these directions. In some embodiments, the longitudinal direction 113 may be described as Y direction 113. The lateral or transverse direction 115 may be described as the X direction 115. The vertical direction 111 may be described as the Z direction 111. The rotational, vertical or other movements can be driven manually or by, for example, one or more motors.

In the example illustrated in FIGS. 4A, 4B and 5, the plane of rotation of the couch 114 is shown as being parallel to the floor. This may commonly be the case but it is not limited to this. The curved rails 122 themselves may be fixed at an incline to the floor or the tilt may actually be altered before, during or after the rotation of the couch 114. Furthermore, the couch 114 may comprise a table top 144 which is itself configured to rotate, for example about the axis of the bore or the longitudinal axis 113. This also serves to minimise the radiation dose received by healthy tissue surrounding a target region.

The rotation of the patient support system 114 can occur before, during or after treatment. Rotation can be continuous or discrete/static. Rotation of the couch 114 may also occur with the table top 144 extended or not extended. Rotation of the couch 114 can also occur at the same time as table top 144 is being extended. In one example, a patient 140 lies on the couch 114 in its non-extended position. The couch 114 is then extended, the patient is scanned and exposed to radiation. The radiation is then stopped, the couch 114 is rotated (yawed) manually by sliding the couch 114 along the curved rail 122 and the patient is then exposed to further radiation. In another example, the radiation is not stopped and the rotation of the couch 114 happens automatically and at the same time as the patient is exposed to radiation.

This rotation may be controller by a processor which may be comprised in the patient support surface 114 or may be found elsewhere. For example, the processor can control the speed of rotation, the angle of rotation or the amount of rotation. This processor may also be used to control the radiation emission, radiotherapy treatment or other operation of the radiotherapy device. This can allow the rotation of the couch 114 to be synchronized with the operation of the radiotherapy device or delivery of the radiotherapy treatment.

In a bore solution, such as that shown in FIGS. 4 and 4A, the rotation of the couch 114 may be inhibited at some angles by the gantry 116 or gantry cover. For example, the couch 114 may be rotated by +/−30° from the neutral position. The neutral position is when the couch 114 is aligned with the axis of the bore and parallel to the floor. When the patient support system 114 is fully extended into the bore, there may be less rotation possible compared to when the patient support system 114 is not extended, or only partially extended, into the bore. As a result, this system is particularly well suited to treatments for head and neck.

The one or more curved rails 122 may be made from the same materials or different materials. For example, each curved rail 122 could be made from a metal, for example steel. The curved rails 122 can be fixed to the floor or another support surface. The rails comprise a track and slider. The slider can be attached to the table top or on the frame. The slide position can be controlled by a linear motor, timing belt or direct drive. A direct drive is a separate cog track or an integrated cog track onto the rail. To help prevent the sliders crabbing between the rails, some flexures can be used to compensate tolerances.

Alternatively, the rotation mechanism 120 may not in fact comprise a curved rail 122 but may comprise one or more curved trenches, with the center of curvature of the one or more curved trenches substantially located at the isocenter 124, wherein the one or more curved trenches serves to guide the rotation of the patient support surface 114 about the isocenter 124. Alternatively, the rotation mechanism 120 may comprise one or more curved rails 122 and one or more curved trenches, with the center of curvature of both substantially located at the isocenter 122. Where the centre of curvature is referred to as being substantially located at the isocenter 122, this includes any point that falls substantially along a vertical axis passing through the isocenter 122, as well as the isocenter 122 itself. Accordingly, it will be apparent that the particular means used to guide the rotation can be varied and the important concept is that the centre of curvature of the rotation guide is located substantially at the isocenter 124.

The radiation source or gantry 116 itself may also be partially rotated about the transverse axis of the short end of the patient support surface 114 in its neutral position, although not necessary when the patient support surface 114 is in its neutral position, either at the same time, or a different time, synchronously or separately to the patient support surface 114.

By using a rotation mechanism 120 comprising curved rails as described, it is possible to cause pure isocenter rotation of the patient support system 114 without the rotation mechanism 120 sharing a common mechanical axis with the gantry 116. In other words, isocenter rotation and the benefits that come with that are achieved whilst keeping the rotation mechanism 120 outside the radiation unit, thereby not interfering with gantry rotation or interfering with the delivery of the radiation. Accordingly, the present disclosure allows the dose received by healthy tissue during radiotherapy treatment to be minimised.

Figure 6:
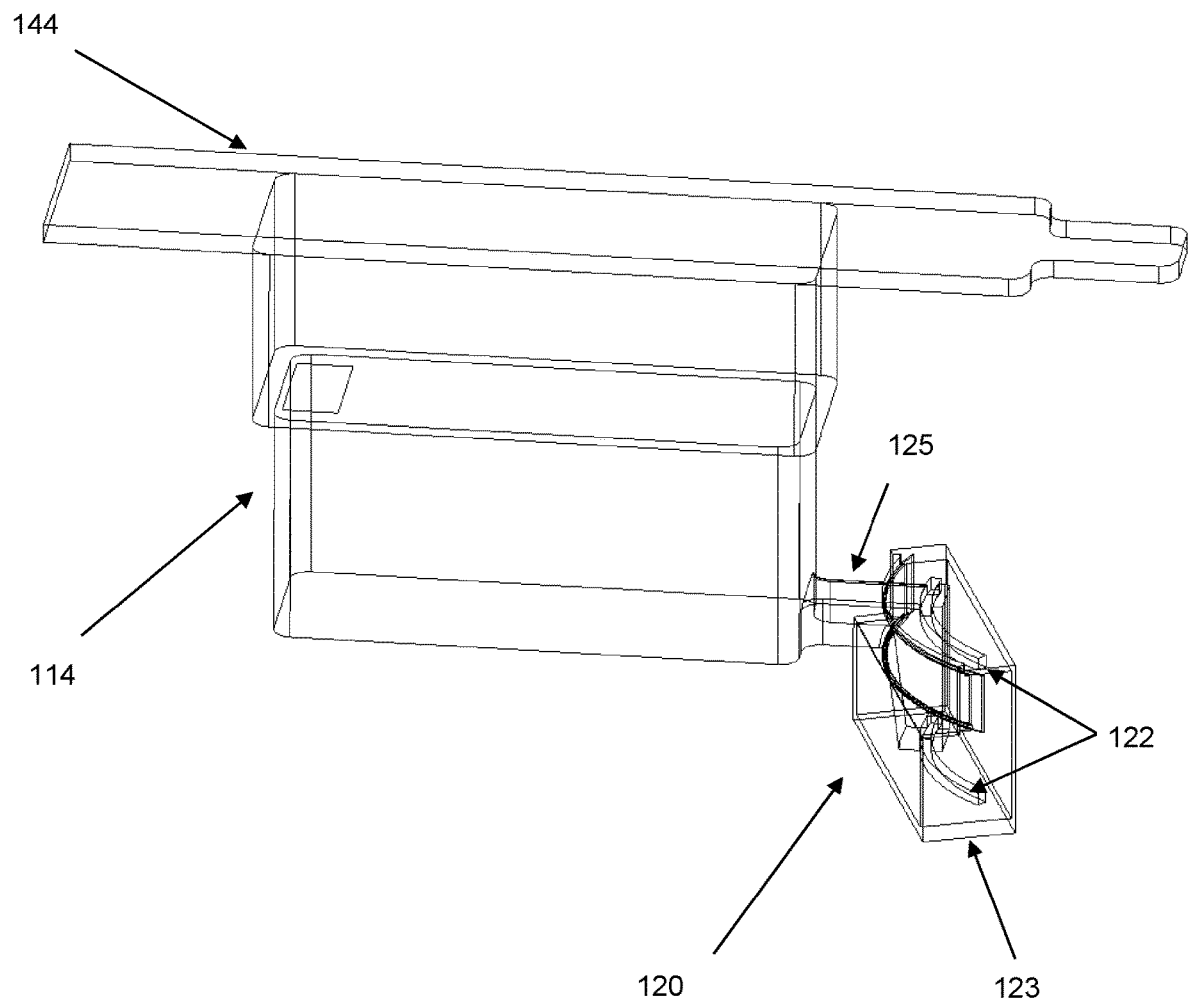
FIG. 6 depicts an isometric view of an embodiment of the radiotherapy device comprising two curved rails aligned vertically.
Figure 7:
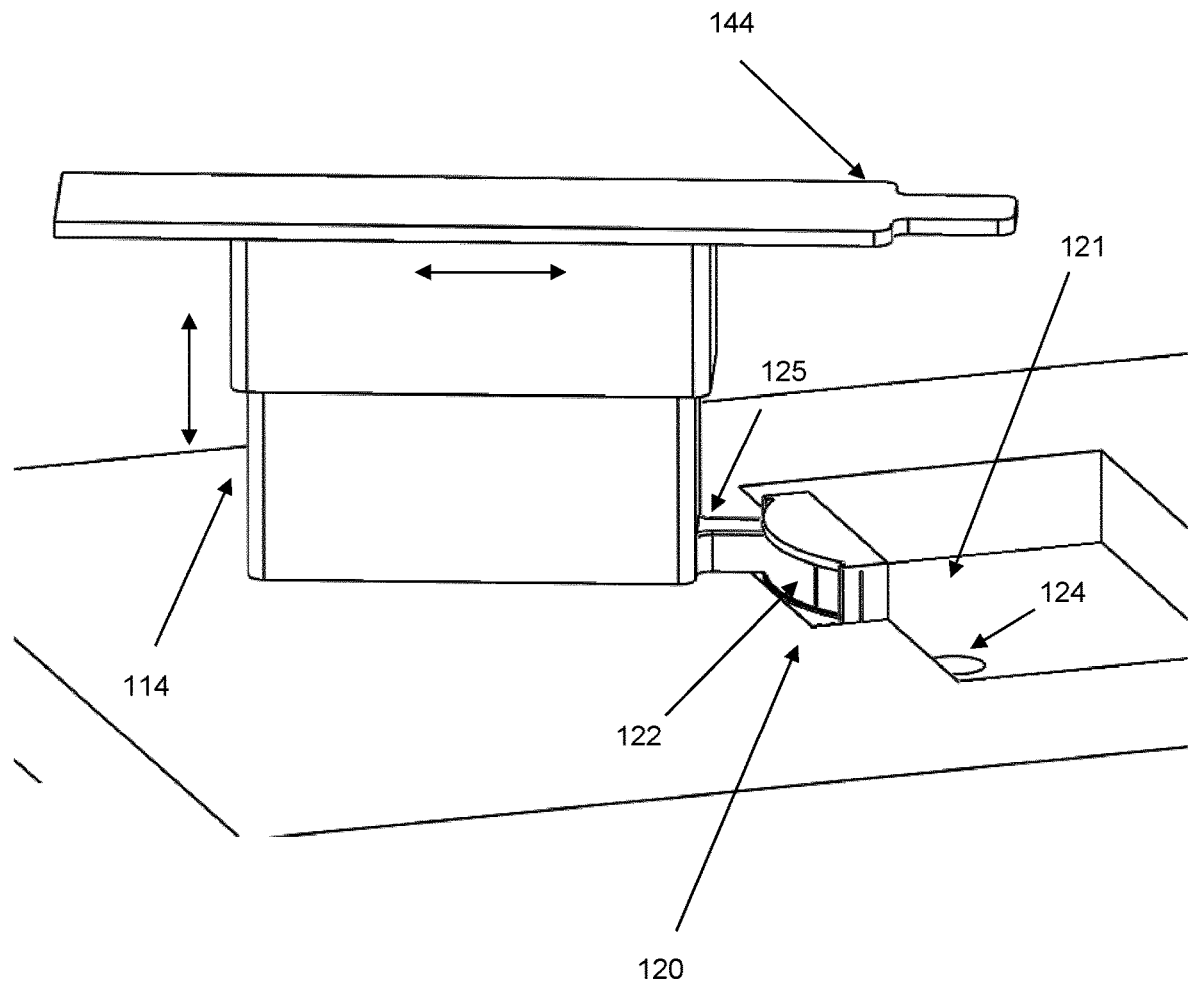
FIG. 7 depicts an isometric view of an embodiment of the radiotherapy device connected to the floor, the radiotherapy device comprising two curved rails aligned vertically.
Figure 8:
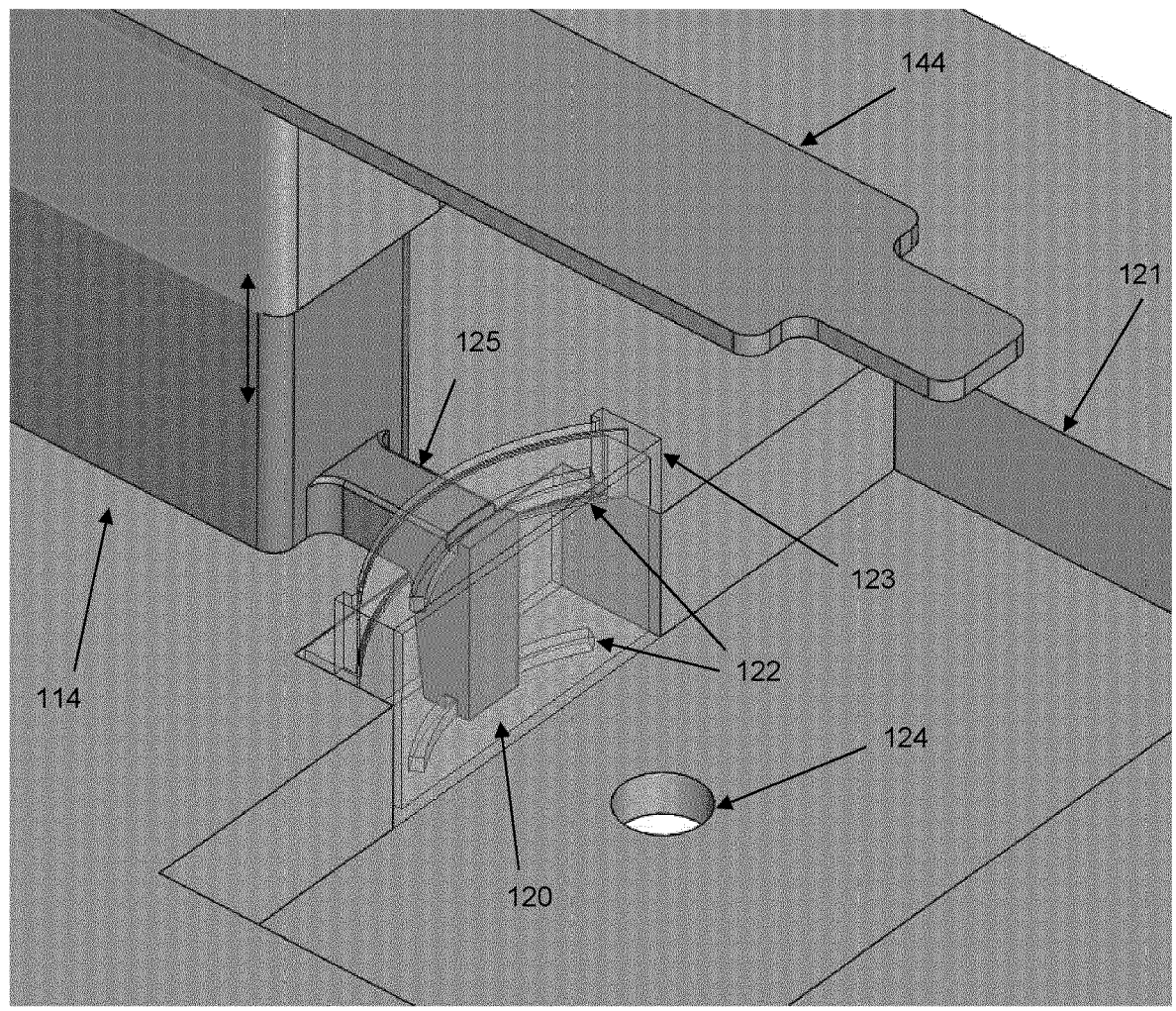
FIG. 8 depicts a detailed isometric view of an embodiment of the radiotherapy device comprising two curved rails aligned vertically.

Another embodiment is shown from three different perspectives in FIGS. 6, 7 and 8. These figures show a patient support surface 114 supported by and connected to a rotation mechanism 120. The couch 114 is connected directly to the rotation mechanism 120 or via an intermediary and can be connected by any suitable means, for example, mechanically. The couch 114 may include a number of rollers, a table top 144, a table base, or other parts. In these figures, the rotation mechanism 120 is connected to the floor and, in particular, within a pit 121 that forms part of the floor but it could be connected to a gantry 116, a wall or other support structure instead or as well. The rotation mechanism 120 is shown as being partly comprised within the pit 121, but may be formed completely inside the pit 121. The rotation mechanism shown in FIGS. 6, 7 and 8 is similar to the rotation mechanism shown in FIGS. 4A, 4B and 5, as discussed above. For example, the rotation mechanism 120 makes use of two curved rails 122, with the centre of curvature for both curved rails 122 being located substantially at the isocenter 124. However, in this embodiment, the curved rails 122 are stacked on top of each other, which is to say that they are parallel with one another but spaced apart from one another in a vertical direction, for example along a vertical axis. The vertical axis 111 is the axis of rotation. The rotation mechanism 120 is shown as being comprised within a box 123.

In this embodiment, the couch 114 is connected to the curved rails 122 by an arm 125. The arm 125 may be connected to the curved rails 122 using any appropriate means. For example, the arm 125 may comprise first and second slots for the first and second curved rails 122 to engage with. The first and second slots may be straight or may be curved with a radius of curvature designed to match the radius of curvature of the curved rails 122. In this example, the arm 125 also acts as the base for the couch 114 but the arm 125 may be separate from the base of the couch 114. In one example, instead of using curved rails 122, curved trenches are used. Any other appropriate curved guide may also be used instead of the curved rails 122 referred to in this disclosure. In another example, a curved trench is used in conjunction with a curved rail 122, both of which have a centre of curvature that is the same and that is located at the isocenter 124 (or a point along a vertical axis passing through the isocenter 124). In another example, the curved rail 122 has a different radius to the curved slot but, the centre of curvature for both of the curved rail 122 and the curved slot is still the same. By separating curved rails 122 (or a curved rail 122 and a curved trench) vertically, the rotation mechanism 120 can be kept compact, thereby saving horizontal space.

Figure 11:
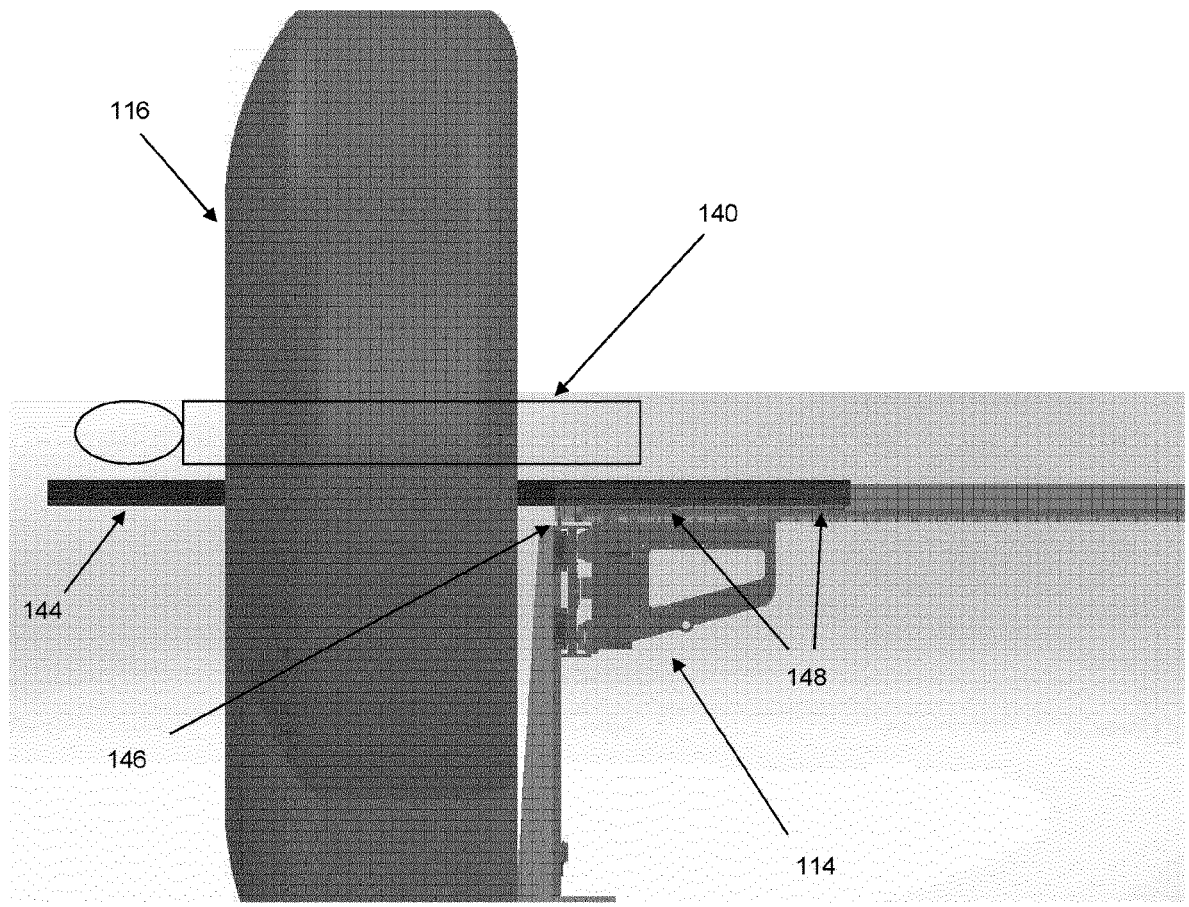
FIG. 11 depicts a side elevation view of an embodiment of the radiotherapy device and illustrates a subject support surface in its loaded and extended position.

As described above, the patient support surface 114 may comprise an extendable table top 144 which can move independently from the rest of the patient support surface 114, such as a table base, and in any direction, for example, a longitudinal direction (along a longitudinal axis 113 of the patient support surface 114). This can be extended from a first position, for example, a position outside the plane of the gantry 116 (as shown in FIG. 9A) to a second position, for example, a position that results in a portion of the couch 114 or table top 144 being inside the plane of the gantry 116 (as shown in FIG. 11). This serves multiple purposes which include enabling a patient 140 to easily climb onto the couch 114 when it is in a first position, before positioning the patient 140 so as to receive the treatment beam 110 in the second position. This extension can also be done to compensate for the movement of the couch 114. This extension can also be performed as part of a spiral treatment, as described in the background section.

Figure 9:
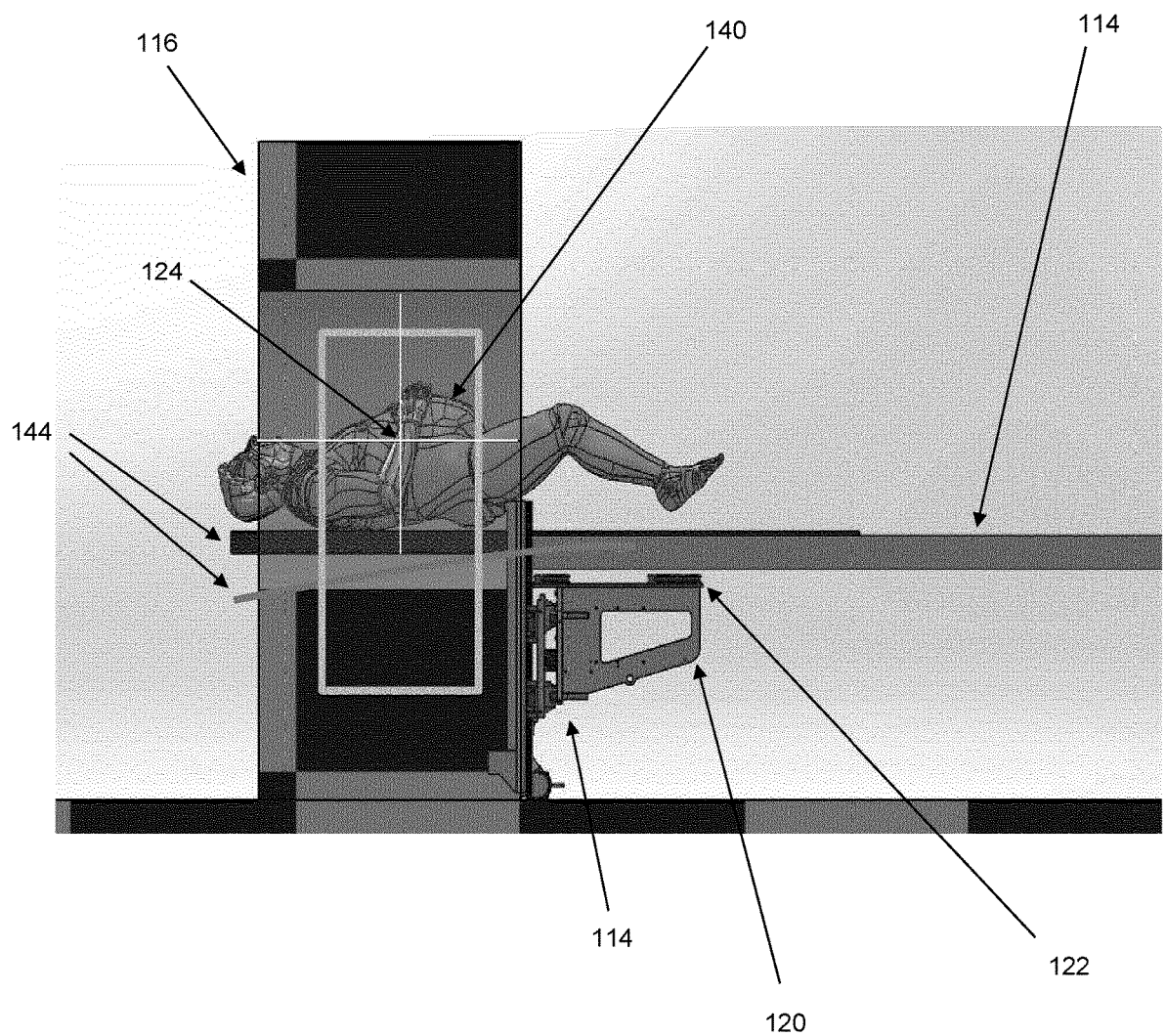
FIG. 9 depicts a side elevation view of an embodiment of the radiotherapy device and illustrates bending of an extendable table top of a patient support surface that is loaded and in its extended position.

As illustrated in FIG. 9, when the table top 144 is in the second (extended) position, the weight of the patient 140, the table top 144 itself or both of these weights, cause the table top 144 to flex (also interchangeably referred to herein as bend or deflect). The amount of flex depicted in FIG. 9 is exaggerated for illustrative purposes. An embodiment of the invention provides a system that allows this table top 144 bending to be compensated for in such a way as to enable the radiation to be more accurately focused on the position of the target region, as shall be explained by reference to the structure and operation of the system below.

Figure 10A:
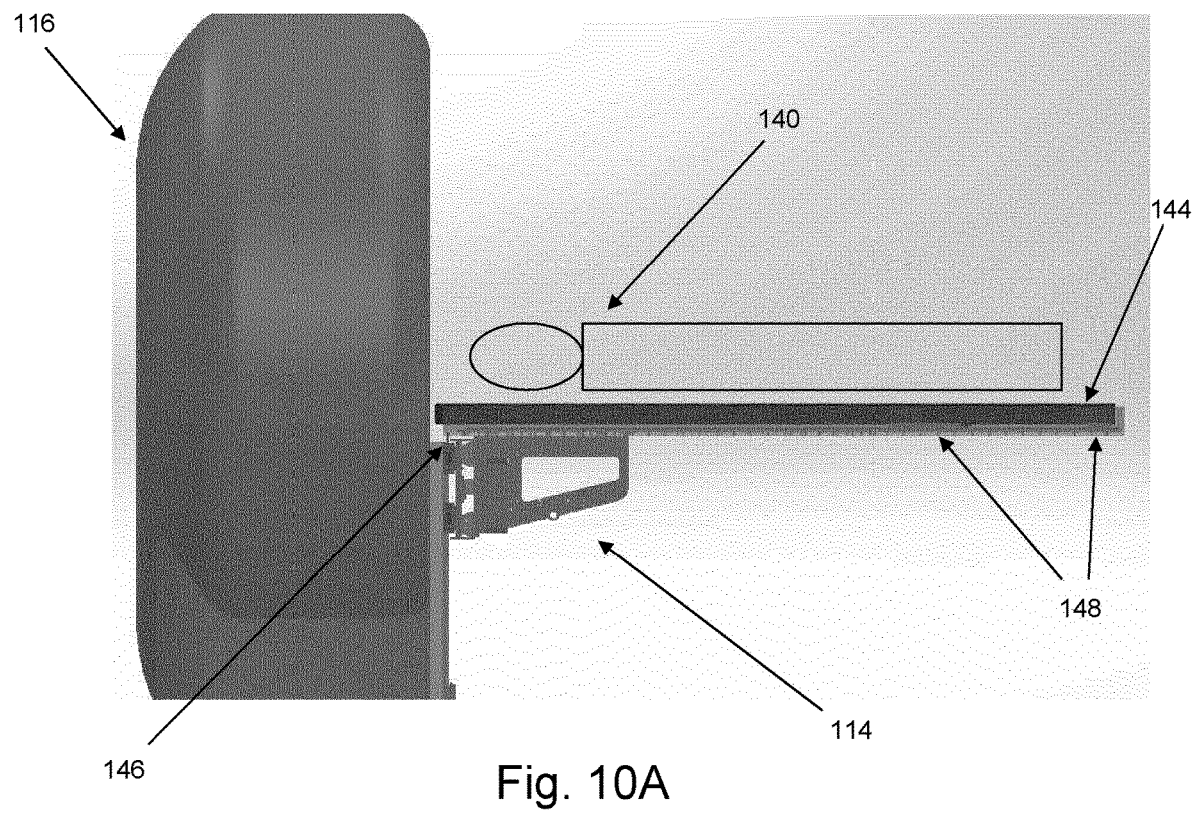
FIG. 10A depicts a side elevation view of an embodiment of the radiotherapy device and illustrates a subject support surface in its loaded and non-extended position.
Figure 10B:
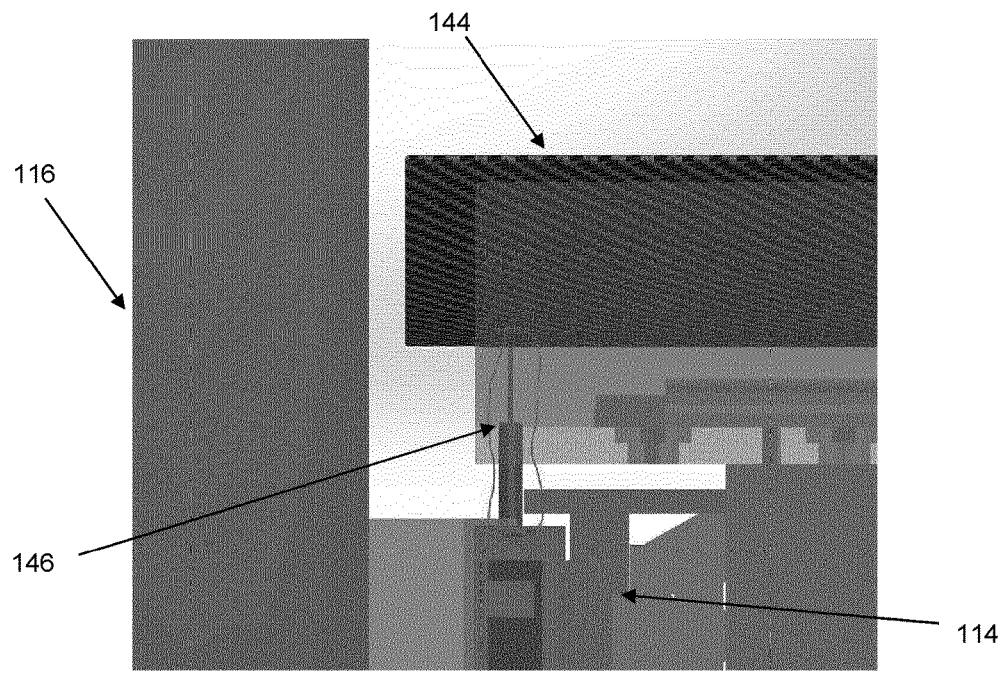
FIG. 10B depicts a close up of a side elevation view of an embodiment of the radiotherapy device and illustrates a position of a sensor with respect to the subject support surface.

FIGS. 10A, 10B and 11 show a system for positioning a subject, such as a patient 140, in a radiotherapy apparatus. The radiotherapy apparatus is similar to that described above in relation to FIG. 3, however, the subject support surface 114 also comprises one or more sensors 146 configured to measure a vertical position of the table top 144. In one embodiment, as depicted in FIGS. 10A, 10B and 11, the subject support surface 114 is connected to the gantry 116 and also comprises the rotation mechanism 120 (in this case one or more curved rails 122) within the subject support surface 114, although it is not necessary for it to comprise any rotation mechanism 120. In this way and in relation to these Figs., the subject support surface 114 refers to everything, including a rotation mechanism 120 (if present), that supports and positions the table top 144 in such a way as to position a subject 140 in such a way as to receive the treatment beam 110. The subject support surface 114 may not be connected to the gantry 116 and be connected to a support surface such as a floor instead. As described previously, the table top 144 can be extended along the longitudinal axis 113 using one or more motors, which can be electric motors with absolute encoders or other encoders, although any other suitable drive mechanism can be used instead of one or more of the one or more motors. The table top 144 itself is supported in exactly the same way in the outer (first, non-extended) position and the inner (second, extended) position, so that the absolute table top 144 flex will be the same over the full stroke (the full range of the extension of the table top 144).

FIG. 10B shows a magnified view of the area comprising the sensor 146. The sensor 146 is located close to the entry of the bore of the gantry 116. Although the embodiment depicted in FIGS. 9, 10A, 10B and 11 is of a radiotherapy apparatus with a bore, the system can also not have a bore and can instead have an open gantry.

The sensor 146 is communicatively coupled to a processor and is configured to send data to the processor either directly or indirectly. In one example, the sensor 146 comprises a linear variable differential transformer (LVDT) that is configured to convert mechanical motion into an electrical current. LVDT sensors are a known technology, the mode of operation of which will not be described here in great detail. However, physically, the LVDT construction is a hollow metallic cylinder in which a shaft of a smaller diameter moves freely along the cylinder's long axis. The sensor 146 also comprises a pressure wheel that contacts the underside of the table top 144 in the first position, in the second position, and at all times in between these positions. As the table top 144 is extended it flexes, as already described above. This results in the pressure wheel being compressed, causing the shaft of the LVDT with the smaller diameter to move inside the larger cylinder which in turn causes an electrical current that corresponds to the displacement of one cylinder relative to the other. In this way, the sensor 146 is used to measure a deflection of the table top 144. Other appropriate sensors can also be used. In particular, other sensors that are known for providing accurate and easy measurements. For example, an alternative sensor could be a laser triangular measurement device of a type well known to the skilled person, so long as it is radiation hard due to the sensor's proximity to the beam in the scatter area. Alternatively, the sensor could comprise one or more ultrasonic sensors. The compression of the sensor 146 is related to a position of the table top 144 which in turn is related to a deflection or bend of the table top 144. Any of these values or an electrical signal that can be used to calculate any of these values, is then communicated to the processor so that the processor can determine the deflection of the table top 146.

The sensor 146 is comprised in the subject support surface 114 so as to only measure table top 144 flex. The sensor 146 is located outside the imaging/radiation volume and is attached to the couch 114 so that, when moving the patient 140 together with the table top 144 into the bore the structural flex of the rest of the couch 114, is not taken into account. In this way, only the table top 144 flex is measured. Whilst only one sensor 146 is depicted, it should be understood that more than one sensor 146 can be used, for example, to provide redundancy. The same lateral position is measured to avoid any variation in measurements caused by lateral motion and/or unsmooth underside of the table top 144.

When the table top 144 is in the second longitudinal position (which is an extended position), there is less bending measured compared to in the first longitudinal position (which is a non-extended position). The amount of bending will be increased at both longitudinal positions when the table top 144 is loaded, i.e. a patient 140 is positioned on the table top 144. In the loaded state, the weight of the patient increases the bending moment on the table top 144. The table top 144 is effectively a cantilever, supported at two points towards one end of the table top. The bending moment will be zero at the free end and it will be maximum towards the supported end. By measuring a deflection of the table top 144 in its first position and also in its second position, the relative deflection, change in deflection and/or increase in deflection can be determined. It should be understood that the deflection is a value that is equivalent to a relative position and is calculated based on a change in the position of the table top 144, in the vertical 111 direction, at the location of sensor 146 along the longitudinal axis 113 between an unloaded reference state and a loaded state and/or between a first position and a second position or, as will be explained below. Furthermore, whilst for simplicity the deflection is discussed here in relation to a first position and a second position, the position of the table top 144 can be measured at more than two positions. For example, the position of the table top 144 can be measured at 5, 10, 100, 1000 or some other number of positions along the extension of the table top 144 along the longitudinal axis 113. As another example, the position of the table top 144 can be measured at different levels of extension along the longitudinal axis 113, for example, every 50 mm, 10 mm, 1 mm or other interval. The position of the table top 144 in the vertical direction, relative to the first position (which is also referred to as the deflection) can therefore be determined for a number of different positions, each corresponding to a particular extension of the table top 144 on a scale from no extension to full or maximum extension, which may refer to the maximum extension used for a particular treatment rather than to a maximum possible extension. In one example, the measurement zone is the full treatment zone and the deflection is measured in at least three different places to determine the tilt angle of the table top 144. When the treatment zone is longer, more measurements can be taken because the tilt angle will vary.

In operation, a patient 140 climbs on to the subject support system 114 when the table top 144 is in its non-extended position. The table top 144, with the patient 140 on it, is then extended into the bore and the table top 144 deflection is then measured at several positions during the transport of the table top 144 into the bore. The amount of deflection (or the vertical position of the table top 144 at the location of the sensor 146) is measured by the sensor 146 at each position and is saved in a memory associated with the processor. In this way, a deflection profile can be generated and recorded by the processor. For example, the profile may resemble a portion of a negative exponential curve or some other shape, as illustrated in FIG. 9.

The subject 140 is then imaged to locate the position of the target region, so that the treatment beam 110 can be focused on this area. The subject support surface 114 can also be controlled and extended in the vertical 111 or lateral 115 direction so that the target region is located at or close to the radiation isocenter 124 or other desired location.

A spiral treatment is then performed in which the table top 144 is retracted (the opposite of the earlier extension) whilst the treatment beam 110 is administered. As the table top 144 is retracted, the deflection of the table top 144 will reduce. The deflection profile that has been determined by the processor is used to predict the changing vertical position of the location of the target region, according to the current level of extension (or amount of retraction). Knowing that the target region is not moving (retracting) perfectly parallel to the axis of the bore 113 but is instead following a particular (e.g. banana shaped) profile relative to the axis of the bore allows the treatment to be adjusted accordingly.

For example, the treatment can be offset in such a way that the radiation isocenter 124 can be kept precisely within the target region over the full distance that the table top 144 moves along the longitudinal axis 113 during the treatment. In one example, the vertical position of the table top 144 can be raised or lowered along the vertical axis 111 to coordinate the absolute vertical position of the table top 144 with the deflection profile so as to maintain the target region substantially at the isocenter and optimise the treatment by reducing the amount of healthy tissue exposed to harmful radiation. This vertical movement is actuated and controlled by the subject support surface 114 which, as described above, is configured to extend the table top 144 along the vertical axis 111. In other words, the treatment can be correlated to, and using, the predicted deflection profile during retraction of the table top 144, which is the reverse of the deflection profile determined during extension of the table top 144. The processor that determines the deflection profile can be used to synchronise the treatment according to the deflection profile or it can supply the information required to do so to another processor that is used to control the treatment. In this way, it is possible to perform an accurate spiral treatment whilst only taking initial images, rather than during the treatment. This reduces the harmful effects of the imaging, whilst also increasing the speed of the treatment.

In one example, a lung spiral treatment is performed using the disclosed apparatus. This treatment is performed by scanning a treatment beam 110 over the target region, starting from towards the end of the patient 140 that comprises the patient's head and moving down the patient's body for a distance of 500 mm. The scanning is achieved by physically moving the patient 140, on the table top 144, through the treatment beam 110, as shall now be explained. In one example, the treatment beam is also moved. For example, a tilted beam can be used.

To get the patient 140 into position, the patient 140 first climbs onto the table top 144 in a first, non-extended longitudinal position. The table top 144 is connected to the couch 114 by two connection points, also referred to as the table top attachment points 148 (although this number may be greater or smaller). These two table top attachment points 148 are fixed on the table top 144 so that the table top 144 is attached by the same two points 148 in both the first position and a second position. However, the connections 148 to the subject support surface 114 are movable from a first longitudinal position to a second longitudinal position relative to the subject support surface 114. This longitudinal movement can be achieved using any appropriate means. For example, the table top 144 may be connected to the couch 114 in such a way as to be configured to move along it in a longitudinal direction along a set of rollers, sliders, or along a rail. The movement along the longitudinal axis 113 from a first position to a second position can be driven manually but can also be driven by, for example, one or more electric motors or by any other suitable means.

The weight of the patient 140 on the table top 144, particularly if the patient 140 is large, will cause the table top 144 to flex by an amount, for example, 3 mm. When the table top 144 has a subject 140 positioned on it, it is to be considered as in a loaded state. The amount of flex will vary along the length of the table top 144, with the flex being greater further along the table top 144 away from the table top attachment points 148. However, once the patient 140 is on the table top 144, if the patient does not move relative to the table top 144, the absolute amount of flex of the table top 144 will not change over the course of the treatment or with the extension of the table top 144. The table top 144 may comprise additional means to prevent the patient 140 from moving on it during the treatment or transport into the bore, for example, straps, blocks, braces or other suitable means. In other words, the flex of the table top 144 as a whole does not change as the table top 144 is extended, but only the amount of flex measured relative to a particular longitudinal point (i.e. relative to the sensor 146).

Before the patient 140 is positioned on the table top 144, the sensor 146 is used to provide a first reference value or signal. This value or signal and the subsequent values or signal generated by the sensor 146 can be considered to be representative of the height of the table top 144 at the position of the sensor 146 in an unloaded state. As the patient 140 is positioned on the table top 144 in its first (non-extended) position (i.e. the loaded state), the table top 144 flexes and the sensor 146 is compressed, resulting in an electric signal or a change in electrical signal that is communicated to the processor so that the processor can determine a new height of the table top 144 and therefore, the amount of deflection caused by the particular patient 140 in the first position along the table top 144. For example, the sensor 146 may determine that there has been a change in height of the table top 144 (in other words a deflection) of 3 mm when comparing the height of the table top 144 with the patient 140 on it in its first position, to the height of the table top 144 without the patient 140 on it in its first position.

In this example, the table top 144 is then extended along the longitudinal axis 113 into the bore so as to position the inferior end of the target region beyond the location that will be the centre of radiation during treatment. At this point, the location of the target region may be known approximately due to previous diagnostics. The approximate position target region may be physically marked on the patient 140 by use of a pen or a tattoo. This can be used to assist the patient 140 being moved to approximately the correct location for receipt of the start of the treatment, for example, manually by an operator. This can be assisted by the use of laser positioning. However, the position of the actual target region can move inside the patient 140 relative to the marked position on the outside of the patient 140 due to swelling or for other reasons. In order to accurately know the position of the target region at the time or nearer to the time of treatment and so that the patient can be precisely positioned and thereby reduce any unnecessary exposure of healthy tissue to the treatment beam, the patient 140 is scanned using an MR imaging apparatus 112 to obtain initial CBCT images. This allows the precise location of the target region to be determined so that the couch 114 can then be adjusted further, for example by extension in a vertical 111, lateral 115 or longitudinal 113 direction so as to precisely position the patient 140 and particularly the target region, relative to the radiation isocenter or isocenter 124. For example, the target region is positioned within 3 mm, 1 mm or 0.1 mm of the desired location. In one example, it is desirable to have the target region within 1 mm of the intended position. The table top extension in this position will be referred to as the second (extended) position, although the second position may also be at a greater extension than that suitable for the start of the treatment. Whilst the table top 144 is in the second position, the sensor 146 will provide a second height measurement for the table top 144 which, when compared with the reference value, enables a deflection of the table top 144 in the second position, at the location of the sensor 146, to be determined. This second deflection can be compared by the processor to the first deflection to determine the change in flex between the first longitudinal position and the second longitudinal position. Because in the second longitudinal position the sensor 146 is measuring the height of the table top 144 at the end of the table top 144 that is closer to the table top attachment points 148, the amount of flex determined for the second longitudinal position is expected to be less than for the first longitudinal position.

Between the first position and the second position, the flex will vary by an unknown amount that will depend on how close the position is to the attachment points 148 of the table top 144 and cannot easily be calculated without knowing the centre of mass of the subject 140, which is something that will vary between subjects 140 and is hard to determine. As a result, the sensor 146 is used to measure the height of the table top 144 at one or more positions (which correspond to different levels of extension of the table top 144 along the longitudinal axis 113) between the first position and the second position. The first position is often the non-extended position and the second position is often the maximally extended position (for that treatment). In this example, the sensor 146 measures the height of the table top 144 for the first 1000 mm of extension, every 1 mm. The sensor 146 data is then used to determine the amount of deflection every 1 mm and, in this way, a deflection profile is generated by the processor. This deflection profile can be generated during or after transport of the table top 144 into the bore (or patient 140 loading).

Having accurately positioned the patient 140 using the CBCT image and the couch 114 and table top 144, the treatment is begun. The treatment beam 110 is turned on, as described previously. Either continuously as the treatment beam is administered, or in one or more intervals between the administering of the treatment beam, the table top 144 is retracted by a distance that corresponds to the desired length of the target region that is receiving the treatment beam, in this case, 500 mm. The deflection profile, saved in the memory associated with the processor, can be used to predict the amount of deflection of the table top 144 and therefore the change in the vertical position of the target region, at any particular time/position of the retraction. For example, if the deflection is 5 mm the vertical movement will raise the couch 114 or the table top 144 by 5 mm to compensate for the deflection.

This allows the treatment to be optimised by compensating for the changing height of the target region as the table top 144 is moved from the second longitudinal position back to the first longitudinal position (or some other position therebetween corresponding to the end of the target region and also referred to here as a third longitudinal position). The treatment can be adjusted by the processor that determines the deflection profile, or the deflection profile can be communicated to a separate processor that is configured to adjust the vertical height according to the deflection profile.

Once the table top 144 has reached the third longitudinal position, the treatment is stopped by turning the beam completely off. The table top 144 is then fully retracted to the first longitudinal position to enable the patient 140 to easily dismount from the couch 114.

In one example, the processor is also configured to take deflection measurements whilst the table top 144 is being retracted. These measurements can be compared to those taken during the extension, to see if the deflection has varied, which could be indicative of a patient 140 having moved. By comparing the deflection at a particular point during retraction of the table top 144 to the corresponding measurement taken at the same point during the extension of the table top 144, a change in deflection value can be calculated. In one example, the processor is configured to stop the radiation if the change in deflection value is greater than a change in deflection safety threshold value. In one example, after the radiation has been stopped in response to the change in deflection value being greater than the change in deflection safety threshold value, the processor is configured to instruct a CBCT scan to accurately check the patient 140 position and, for example, recalibrate the position of the target region accordingly. In one other example, in response to the change in deflection value being greater than the change in deflection safety threshold value, the processor is configured to alter the treatment in such a way as to compensate for the change in deflection caused by, for example, the movement of a patient 140.

The sensor 146 that is measuring table top 144 position and flex needs to be fast and accurate. For example, the sensor can have an accuracy of around 0.1 mm or better to help ensure the tolerance is a reasonable level. As described above, an LVDT sensor can be used in which a magnet is moved inside a coil. LVDT don't have electronics near the sensor and are simple. As described above, the LVDT, for example an induSENSOR LVDT, may comprise a pressure wheel or a standard roller that is built into the LVDT. Alternatively, a triangulation sensor or a proximity sensor can be used. Any other appropriate type of sensor could also be used as the sensor 146, as long as it is capable of accurately determining the position or deflection of the table top 144. More than one sensor 146 can also be used to provide redundancy, to increase the reliability of the measurements and the deflection profile, or for any other reason. In one example, multiple sensors 146 are located along the lateral axis 115 of the couch 114 and are configured to determine a deflection of the table top 144 in the lateral direction. If multiple sensors 146 are used, the sensors 146 can be the same kind or could be different from each other. In one example, the one or more sensors 146 are chosen to be radiation hard to prevent damage from scattered radiation from the linac and CBCT over time.

The table top 144 is made from one or more rigid materials such as steel, aluminium, titanium, a composite or any other suitable material. The table top 144 may also comprise a softer material such as a foam, designed to improve the comfort or support of the patient 140. The table top 144 may also comprise multiple layers, one of which includes a plastic. In one example, these materials are chosen to be radiation hard to prevent them from becoming damaged or brittle following repeated exposure to emitted radiation.

Whilst the materials chosen for the table top 144 will be chosen to provide an adequate degree of rigidity, the system disclosed allows the materials use to be less rigid than would otherwise be required in a radiotherapy apparatus without table top 144 bending compensation. This is because the bending caused by a choice of less rigid materials can nonetheless be compensated for by adjusting the radiotherapy or other treatment, as described above. This results in a wider range of materials being suitable for use in the table top 144. For example, materials that are less rigid but cause less interference to the radiation can be used. This in turn reduces the amount of radiation that has to be generated, thereby saving power and minimising the damage done to any healthy tissue exposed to the radiation. Furthermore, rigid materials are often expensive and reducing the requirements for rigidity enables cheaper or more commonly available materials to be used for the table top 144.

It is possible to mount more sensors to also measure the flex of the main body of the subject support surface 114, but this flex will be less great than the table top flex. The structural flex will depend on the couch 116/table top 144 position in the longitudinal direction 113. There will be a flex in the main structure of the couch 116 that is related to the rigidity of the materials used for its construction, which is why rigid materials are desirable. However, the majority of the flex still comes from the deflection of the table top 144. In one example, markers are added on to the table top 144 and this is then measured with cameras. For example, the camera or cameras could be placed on the floor and look upwards to the underside of the table top 144, or could look from the side to determine the deflection. The camera need to process high resolution images to get the accuracy of the measurements and the determination of the deflection to within a range of 0.1 mm. In another example, a C-Rad scanner system is used to measure the deflection.

The processor may also be configured to use data from a memory that stores information such as the dimensions and configuration of the components so that these can be used in the calculations controlling the movement of the assorted components and to prevent, for example, the couch 114 from colliding with the gantry 116.

It should be noted that the various embodiments may be implemented in hardware, software or a combination thereof. The various embodiments and/or components, for example, components and controllers for these, also may be implemented as part of one or more computers or processors or field-programmable gate arrays (FPGAs). The computer or processor or FPGA may include a computing device, an input device, a display unit and an interface, for example, for accessing the Internet. The computer or processor may include a microprocessor. The microprocessor may be connected to a communication bus. The computer or processor or FPGA may also include a memory. The memory may include Random Access Memory (RAM) and Read Only Memory (ROM). The computer or processor or FPGA further may include a storage device, which may be a hard disk drive or a removable storage drive such as an optical disk drive, and the like. The storage device may also be other similar means for loading computer programs or other instructions into the computer or processor.

As explained above, the system allows treatments such as spiral treatments to be performed accurately without the need for re-imaging the patient 140 during the treatment (such as re-imaging the patient 140 after the table top 144 has been partially retracted which may otherwise be done). The system is also useful for long field treatments where a table shift is needed to be able to radiate the whole target region because it increases the accuracy of the knowledge of the position of a target region as the table top 144 is moved from one position to another. Getting the couch 114 into the correct position directly before performing the CBCT scan will save time, so table corrections will not be needed after the CBCT scan. The system is also well suited for couches 116 that do not have six degrees of freedom of movement. Re-imaging the patient 140 is harmful to the patient 140 and so alleviating the need for re-imaging reduces the harm done to the patient 140 thereby improving his or her wellbeing. What is more, re-imaging may require the movement of the table to be stopped and will add additional time and costs to the treatment. Removing the requirement for re-imaging therefore increases the speed at which a treatment can be performed, thereby increasing patient 140 throughput and improving the efficiency of the radiotherapy apparatus. The system also enables the position of the target region to be known with greater certainty and accuracy, which enables the treatment to be performed with greater accuracy and confidence in treating the target region. This also minimises the radiation received by healthy tissue.

The invention claimed is:

1. A radiotherapy apparatus for delivering radiation to a subject, the radiotherapy apparatus comprising:
 a source of radiation configured to rotate about an isocenter and emit radiation in a radiation plane containing said isocenter;
 a subject support surface configured such that at least a portion of the subject support surface can be located substantially at the isocenter; and
 a subject support surface rotation mechanism configured to rotate the subject support surface about an axis of rotation that passes through the isocenter, wherein the subject support surface rotation mechanism is located outside the radiation plane, wherein the subject support surface rotation mechanism comprises a first curved guide with a center of curvature located at a vertical axis defined to pass through the isocenter, wherein the radiotherapy apparatus comprises a gantry, and wherein the first curved guide is connected to the gantry.

2. The radiotherapy apparatus of claim 1, wherein the axis of rotation is at least one of a longitudinal axis, a transverse axis or a vertical axis.

3. The radiotherapy apparatus of claim 1, wherein the subject support surface rotation mechanism is configured to rotate the subject support surface before, after, or during a treatment.

4. The radiotherapy apparatus of claim 1, wherein the radiotherapy apparatus further comprises:
a bore for receiving the subject.

5. The radiotherapy apparatus of claim 1, wherein the subject support surface rotation mechanism further comprises:
a second curved guide, wherein a center of curvature of at least one of the first curved guide or the second curved guide is located at a vertical axis that passes through the isocenter.

6. The radiotherapy apparatus of claim 5, wherein at least one of the first curved guide or the second curved guide is aligned within a horizontal plane that is perpendicular to a vertical axis.

7. The radiotherapy apparatus of claim 5, wherein the first curved guide and the second curved guide are spaced apart from each other in a vertical direction.

8. The radiotherapy apparatus of claim 7, wherein the first curved guide and the second curved guide are aligned along a vertical axis.

9. The radiotherapy apparatus of claim 5, wherein at least one of the first curved guide or the second curved guide are formed as first a first curved guide rail and a second curved guide rail.

10. The radiotherapy apparatus of claim 9, wherein at least one of the first curved guide rail or the second curved guide rail are connected to the gantry.

11. The radiotherapy apparatus of claim 5, wherein at least one of the first curved guide or the second curved guide are formed as first and second curved trench guides.

12. The radiotherapy apparatus of claim 1, wherein the subject support surface rotation mechanism is configured to rotate the subject support surface an angle in a range between+/−20 degrees and 40 degrees about the axis of rotation.

13. The radiotherapy apparatus of claim 1, wherein the subject support surface comprises:
an extendable table top; and
a sensor configured to measure a vertical position of the extendable table top, and wherein the radiotherapy apparatus comprises:
a processor configured to:
determine a deflection of the extendable table top using the measured vertical position; and
control a treatment using the radiotherapy apparatus according to the deflection.

14. A method for controlling a subject support surface in a radiotherapy apparatus comprising a source of radiation configured to rotate about an isocenter and emit radiation in a radiation plane containing said isocenter, the method comprising:
providing a subject support surface configured such that a portion of the subject support surface can be located substantially at the isocenter; and
rotating the subject support surface about an axis of rotation that passes through the isocenter using a subject support surface rotation mechanism connected to the subject support surface, wherein the subject support surface rotation mechanism is located outside the radiation plane, wherein the subject support surface rotation mechanism comprises a first curved guide with a center of curvature located at a vertical axis defined to pass through the isocenter, wherein the radiotherapy apparatus comprises a gantry, and wherein the first curved guide is connected to the gantry.

15. A radiotherapy apparatus for delivering radiation to a subject, the radiotherapy apparatus comprising:
a source of radiation configured to rotate about an isocenter and emit radiation in a radiation plane containing said isocenter; and
a subject support surface including a portion configured to be located substantially at the isocenter, the subject support surface comprising:
a subject support surface movement mechanism configured to rotate the subject support surface about an axis parallel to an axis that passes through the isocenter, wherein the subject support surface movement mechanism is located outside of the radiation plane, wherein the subject support surface movement mechanism comprises a first curved guide with a center of curvature located at a vertical axis defined to pass through the isocenter, wherein the radiotherapy apparatus comprises a gantry, and wherein the first curved guide is connected to the gantry.

16. A non-transitory machine-readable medium with instructions stored thereon, which, when executed by a processor of a computing device, cause the processor to:
control a radiotherapy apparatus, the radiotherapy apparatus comprising:
a source of radiation configured to rotate about an isocenter and emit radiation in a radiation plane containing said isocenter;
a subject support surface configured such that at least a portion of the subject support surface can be located substantially at the isocenter; and
a subject support surface rotation mechanism configured to rotate the subject support surface about an axis of rotation that passes through the isocenter, wherein the subject support surface rotation mechanism is located outside the radiation plane, wherein the subject support surface rotation mechanism comprises a first curved guide with a center of curvature located at a vertical axis defined to pass through the isocenter, wherein the radiotherapy apparatus comprises a gantry, and wherein the first curved guide is connected to the gantry.

17. A system for positioning and rotating a subject in a radiotherapy apparatus, the system comprising:
a source of radiation configured to rotate about an isocenter and emit radiation in a radiation plane containing said isocenter;
a subject support surface configured such that at least a portion of the subject support surface can be located substantially at the isocenter, the subject support surface comprising:
an extendable table top;
one or more sensors configured to measure a vertical position of the extendable table top;
a subject support surface rotation mechanism configured to rotate the subject support surface about an axis of rotation that passes through the isocenter, wherein the subject support surface rotation mechanism is located outside the radiation plane, wherein the subject support surface rotation mechanism comprises a first curved guide with a center of curvature located at a vertical axis defined to pass through the isocenter, wherein the radiotherapy apparatus comprises a gantry, and wherein the first curved guide is connected to the gantry; and a processor configured to:
  determine a deflection of the extendable table top using the measured vertical position;
  control rotation of the subject support surface using the subject support surface rotation mechanism; and
  adjust one or more treatment parameters based on the determined deflection during rotation of the subject support surface.

* * * * *